US009187511B2

(12) United States Patent
Gatineau et al.

(10) Patent No.: US 9,187,511 B2
(45) Date of Patent: Nov. 17, 2015

(54) TITANIUM-ALUMINUM ALLOY DEPOSITION WITH TITANIUM-TETRAHYDROALUMINATE BIMETALLIC MOLECULES

(71) Applicant: L'Air Liquide, Société Anonyme pour l'Etude et l'Exploitation des Procédés Georges Claude, Paris (FR)

(72) Inventors: Julien Gatineau, Tsuchiura (JP); Satoko Gatineau, Tsuchiura (JP); Jean-Marc Girard, Tokyo (JP); Changhee Ko, Tsukuba (JP)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 339 days.

(21) Appl. No.: 13/780,212

(22) Filed: Feb. 28, 2013

(65) Prior Publication Data

US 2013/0295298 A1  Nov. 7, 2013

Related U.S. Application Data

(60) Provisional application No. 61/640,954, filed on May 1, 2012.

(51) Int. Cl.
*C07F 19/00* (2006.01)
*C07F 5/06* (2006.01)

(52) U.S. Cl.
CPC .................. *C07F 19/005* (2013.01); *C07F 5/06* (2013.01)

(58) Field of Classification Search
None
See application file for complete search history.

(56) References Cited

PUBLICATIONS

Sizov et al. "Synthesis and properties of unsolvated bis(cyclopentadienyl titanium alumohydride. Structure of {[(n5-C5H5)2Ti(u-H0]2[(n5-C5H5)Ti(u-H2]Al3(u-H4)(H)}2C6H6 a 12-nuclear titanium aluminum hydride complex with a short Al-Al-bond length and refined structure of LiAlEt4" Jo. of Organo Chem. vol. 603, Iss 2, May 29, 2000, p. 167-173.*
Chokwatvikul, C. et al., "Effect of nitrogen partial pressure on characteristic and mechanical properties of hard coating TiAlN film," Journal of Metals, Materials and Minerals (2011), vol. 21, No. 1, pp. 115-119.
Girolami, G.S. et al., Low temperature MOCVD routes to thin film transition metal precursors, Mat. Res. Soc. Symp. Proc 1998, vol. 168, pp. 319-329.
Qu, X.X. et al., "Characterization of TiAl alloy films for potential application in MEMS bimorph actuators," Materials Science in Semiconductor Processing 5 (2002), pp. 35-38.
Sizov, A.I. et al., "Bis(cyclopentadienyl)titanium tetrahydroaluminates," Koordinatsionnaya Khimiya (1985), vol. 11, issue 3, pp. 339-345, CODEN: KOKHDC, ISSN: 0132-344X, English abstract downloaded from https://www.cas.org/products/scifinder on Feb. 27, 2013.
Subramanian, B. et al., "A comparative study of titanium nitride (TiN), titanium oxy nitride (TiON) and titanium aluminum nitride (TiAlN), as surface coatings for bio implants," Surface and Coatings Technology 205 (2011), pp. 5014-5020.

* cited by examiner

*Primary Examiner* — Mandy Louie
(74) *Attorney, Agent, or Firm* — Patricia E. McQueeney

(57) ABSTRACT

Disclosed are titanium-tetrahydroaluminates precursors, their method of manufacture, and their use in the deposition of titanium-aluminum-containing films. The disclosed precursors have the formulae $Ti(AlH_4)_3$—X, $Ti(AlH_4)_2L$ and $Ti(AlH_4)L_2$. The disclosed precursors may be used to deposit pure titanium-aluminum (TiAl), titanium-aluminum nitride (TiAlN), titanium-aluminum carbide (TiAlC), titanium-aluminum carbonitride (TiAlCN), titanium-aluminum silicide ((TiAl)Si), titanium-aluminum siliconitride ((TiAl)SiN), titanium-aluminum boron ((TiAl)B), titanium-aluminum boron nitride ((TiAl)BN), or titanium-aluminum oxide (TiAlO). or any other titanium-aluminum-containing films. The titanium-aluminum-containing films may be deposited using the disclosed precursors in thermal and/or plasma-enhanced CVD, ALD, pulse CVD or any other type of depositions methods.

16 Claims, No Drawings

TITANIUM-ALUMINUM ALLOY DEPOSITION WITH TITANIUM-TETRAHYDROALUMINATE BIMETALLIC MOLECULES

CROSS-REFERENCE TO RELATED APPLICATIONS

This application claims benefit under 35 U.S.C. §119(e) to provisional application No. 61/640,954, filed May 1, 2012, the entire contents of which are incorporated herein by reference.

TECHNICAL FIELD

Disclosed are bimetallic titanium-tetrahydroaluminate-based precursors, their synthesis, and their use for the vapor deposition of films containing titanium and aluminum.

BACKGROUND

Chemical vapor deposition (CVD) and atomic layer deposition (ALD) have been applied as main deposition techniques for depositing thin films for semiconductor devices because it enables the achievement of conformal films (metal, oxide, nitride . . . etc) through fine tuning of parameters during the process. The film growth is mainly controlled by the chemical reaction of metal-organic compounds (precursors), so the development of optimum precursors is essential under prediction of its property and reaction process. Precursors have been developed to reach required properties based on its specific application to certain types of film.

Titanium and aluminum based films find many different applications useful for the fabrication of nano-devices, such as semi-conductor devices, Microelectrochemical systems (MEMS) devices, or photovoltaic devices, but also in manufacturing of tools or machines. In semiconductor applications, the use of TiAl(N) (titanium-aluminum-nitride) layers is considered for its high oxidation resistance, as well as the low resistivity of such materials. TiAl or TiAlON could replace advantageously TiN films for NMOS metal gate electrode. Kesapragada et al., High-k/Metal Gate Stacks in Gate First and Replacement Gate Schemes, ASMC 2010, pp. 256-259; Miyoshi et al., Titanium-aluminum Oxynitride (TAON) as High-k Gate Dielectric for Sub-32 nm CMOS Technology, Microelectronic Engineering 87 (2010) 267-270. Used as a diffusion barrier between copper and low-k, TiAlN alloy also proved to exhibit very good blocking properties up to 1000° C. Lee et al., Study of Diffusion Barrier Properties of Ternary Alloy $(Ti_xAl_yN_z)$ in $Cu/Ti_xAl_yN_z/SiO_2/Si$ Thin Film Structure, Materials Science in Semiconductor Processing 3 (2000) 191-194. Kawata et al. evaluated the structural, mechanical, and chemical properties of $Ti_{0.58}Al_{0.42}N$ (upper)/TiN (lower films), revealing high oxidation resistance, a low friction coefficient, and high wear resistance. Characterization of (Ti,Al)N Films Deposited by Pulsed D.C. Plasma-Enhanced Chemical Vapor Deposition, Thin Solid Films 386, 2001, 271-275.

Deposition of titanium-aluminum (TiAl) alloy may be used as bimorph actuators in MEMS devices. Qu et al., Characterization of TiAl Alloy Films for Potential Application in MEMS Bimorph Actuators, Materials Science in Semiconductor Processing 5 (2002) 35-38. The advantage of TiAl over aluminum (Al) for this application stems in the instability and high stress gradient of Al.

TiAl(N) films are also of interest for hard coating applications in the tooling or machining manufacturing area because of the high wear and oxidation resistance properties. Chokwatvikul et al., Effect of Nitrogen Partial Pressure on Characteristic and Mechanical Properties of Hard Coating TiAlN Film, Journal of Metals, Materials and Minerals, Vol. 21, No. 1, pp. 115-119, 2011. Still in the coating area, but for bio implants applications, it was observed that TiAlN films exhibited superior electrochemical corrosion resistance compared to TiON and TiN. Subramanian et al., A Comparative Study of Titanium Nitride (TiN), Titanium Oxynitride (TiON), and Titanium Aluminum Nitride (TiAlN), as Surface Coatings for Bio Implants, Surface & Coatings Technology 205 (2011) 5014-5020.

The interest for TiAl-based materials is thus very high. Besides, the need is clearly directed to nano-devices, where depositions of films of a few Angstroms thickness in very constraining geometries, including deep trenches or 3D geometries, are needed. Deposition methods that allow deposition and control at the atom level are desired. Techniques using vapors of organometallic molecules, also called precursors, in Chemical Vapor Deposition (CVD) and Atomic Layer Deposition (ALD) modes are considered to be effective methods to fulfill these needs.

However, available precursors suitable for such vapor phase deposition are relatively scarce. Two different approaches could be considered to deposit TiAl-based films: reaction of two distinctive molecules of titanium (Ti) and aluminum (Al) or usage of a single molecule, intrinsically containing Ti and Al.

The first approach has the advantage of providing better individual control of the deposition parameters, but some issues such as the non-overlapping of two process windows based on both precursors' process windows may occur. Such kind of issues could be solved by using a single source molecule, a bi-metallic precursor containing Ti and Al.

The issue with such molecules is the very limited availability of molecules possessing qualities to be used in gas phase depositions. Namely, the scarcity, proven by the lack of the corresponding literatures, of bi-metallic precursors that possess all or most of the following properties: liquid, sufficiently volatile, stable at storage and delivery conditions, reactive to heat or to other reactants (such as hydrogen ($H_2$), ammonia ($NH_3$), hydrazine ($N_2H_4$), etc), among others.

Ideally the molecules would not be composed of carbon, or would have as little metal to carbon bonds as possible. The way the ligand is linked to the metal atom is also of high importance, as the lower the bond energy between the metal and ligand, the easier the bond will be broken, potentially leading to impurity-free film, as long as the ligand does not decompose itself during the deposition process.

The number of molecules answering to this criterion is limited. Tris(tetrahydroborate)titanium $(TiBH_4)_3$ would be of interest but is reported to be unsuitable for CVD applications because it decomposes thermally at −50° C. Girolami et al., Low Temperature MOCVD Routes to Thin Films from Transition Metal Precursors, Mat. Res. Soc. Symp. Proc. Vol. 168, 1990. However, the stability of this molecule increases by the addition of donor molecules. The 1,2-dimethoxyethane adduct $Ti(BH_4)_3(dme)$ is reported to be stable at room temperature and sublimes readily. Chemical vapor deposition using this precursor gives thin films of $TiB_2$ at temperatures as low as 250° C. Id.

Some other molecules are also described, such as $Cp_2Ti(AlH_4)$. Abstract of Koordinatsionnaya Khimiya (1985), 11 (3), 339-45.

In conclusion, a need remains for molecules with satisfactory properties that allow the deposition of good quality TiAl-based films using single source bi-metallic TiAl precursors.

NOTATION AND NOMENCLATURE

Certain abbreviations, symbols, and terms are used throughout the following description and claims, and include:

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a n-propyl group; the abbreviation "iPr" refers to an isopropyl group; the abbreviation "Bu" refers to butyl (n-butyl), the abbreviation "tBu" refers to a tert-butyl; the abbreviation "sBu" refers to a sec-butyl; the abbreviation "iBu" refers to an iso-butyl; the abbreviation "ph" refers to a phenyl; the abbreviation "Cp" refers to cyclopentadienyl; the abbreviation "Cp*" refers to pentamethylcyclopentadienyl; the abbreviation "Op" refers to pentadienyl; the abbreviation "CHDI" refers to cyclohexadienyl; the abbreviation "HDI" refers to hexadienyl; the abbreviation "AMD" refers to amidinate; the abbreviation "fAMD" refers to formamidinate; the abbreviation "Si-amd" refers to Sillyl amidinate (R1-N=SiR2-NR3); the abbreviation "EDA" refers to dialkyl-ethylenediamine; the abbreviation "DAD" refers to diimine; the abbreviation "MDAD" refers to methyl-diimine; the abbreviation "DMDAD" refers to dimethyl-diimine; the abbreviation "DAAB" refers to di(alkylamino)alkylboron; the abbreviation "DAAA" refers to di(alkylamino)alkylalumium; the abbreviation "DAAG" refers to di(alkylamino)alkylgallium; the abbreviation "Nac-Nac" refers to β-diketimine; the abbreviation "acNac" refers to β-diketonate; the abbreviation "acac" refers to acetyacetonate; the abbreviation "THF" refers to tetrahydrofuran; the abbreviation "dme" for dimethoxyethane; the abbreviation "NHCs" refers to N-heterocyclic carbenes (an Imidazol-2-ylidenes).

The standard abbreviations of the elements from the periodic table of elements are used herein. It should be understood that elements may be referred to by these abbreviations (e.g., Ti refers to titanium, Al refers to aluminum, Si refers to silicon, C refers to carbon, etc.).

A specific care is attributed to describe the ligand DAD. As used herein, the abbreviation "DAD" refers to 1,4-diaza-1,3-butadiene ligand, an α-diimine which has general structure of $R_1$—N=$CR_3$—$CR_4$=N—$R_2$, wherein each $R_1$ to $R_4$ is independently selected from: H; C1-C6 linear, branched, or cyclic alkyl or aryl group; C1-C6 linear, branched, or cyclic alkylamino group such as NRR', where R and R' are independently selected from H or C1-C6 linear, branched, or cyclic alkyl or aryl group; C1-C6 linear, branched, or cyclic fluoroalkyl group (in which some or all of the substituents are F, i.e. partially or totally fluorinated); or an alkoxy substituent such as OR, where R is selected from H or a C1-C6 linear, branched, or cyclic alkyl or aryl group.

Diazabutadiene (DAD) ligands are α-diimine ligands that may be used under different reduction states. The DAD ligand may be selected from one of three reduced forms, with each form determining the bonding mode between the center element (M) and the DAD ligands. As used herein, three different reduction states of the ligand are described as i) neutral, ii) mono-anionic, and iii) dianionic. One of ordinary skill in the art will recognize that the location of the double bonds in the diazabutadiene ligand changes based upon the reduction state of the ligand, as shown below:

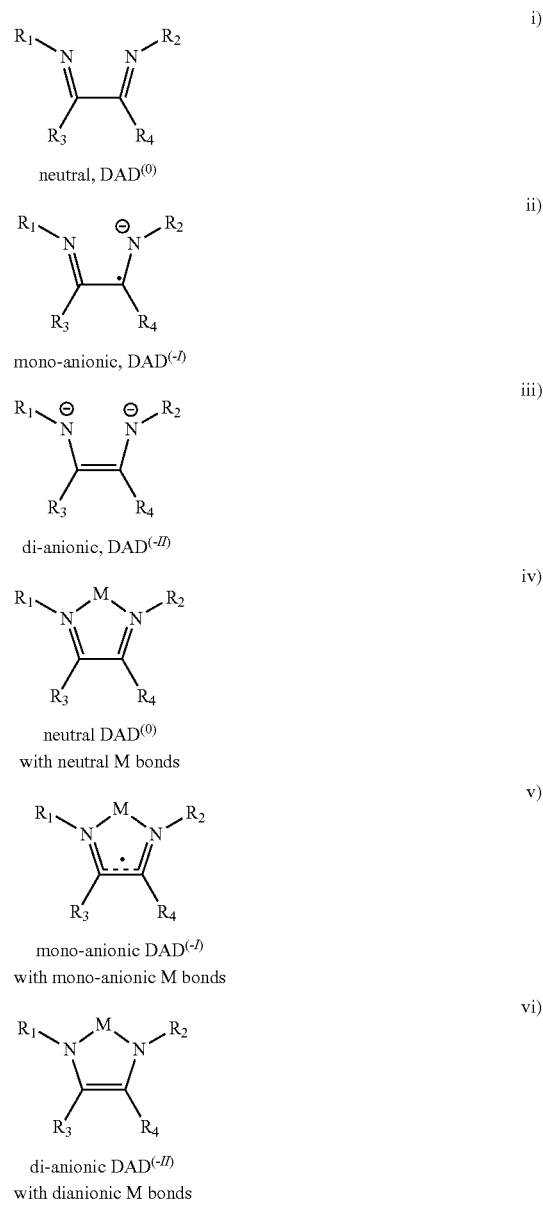

For the sake of simplicity, only the abbreviation "DAD" will be used and is considered to represent at least one of the above-described DAD ligands.

In Table 1, a non-exhaustive list of some ligands proposed for use in this invention, as well as their abbreviation and the way the ligands are written in this document:

TABLE 1

List of the ligand proposed for use and their nomenclature

| | General structure | Example |
|---|---|---|
| Ligand structure | [cyclic structure with R1, R2, R3, R4, R5, R6, R7] | [cyclic structure with Me groups] |
| Nomenclature | CHDI | Me₃—CHDI |
| Ligand structure | R2—N=C(Me)—N—R1 | iPr—N=C(Me)—N—iPr |
| Nomenclature | AMD | iPr₂—AMD |
| Ligand structure | R2—N=C(H)—N—R1 | iPr—N=C(H)—N—iPr |
| Nomenclature | fAMD | iPr₂—fAMD |
| Ligand structure | R3—N=Si(R2)—N—R1 | iPr—N=Si(Me)—N—iPr |
| Nomenclature | SiAMD | iPr₂—SiAMD |
| Ligand structure | R3—N=B(R2)—N—R1 | iPr—N=B(H)—N—iPr |
| Nomenclature | DAAB | iPr₂—DAAB |
| Ligand structure | R3—N—Al(R2)—N—R1 | iPr—N—Al(H)—N—iPr |
| Nomenclature | DAAA | iPr₂—DAAA |
| Ligand structure | R3—N—Ga(R2)—N—R1 | iPr—N—Ga(H)—N—iPr |
| Nomenclature | DAAG | iPr₂—DAAG |
| Ligand structure | R1—N—N—R2 with R3, R4 | Me—N—N—Me |
| Nomenclature | DAD | Me₂—DAD |
| Ligand structure | R1—N—N—R2 with R3, Me | iPr—N—N—iPr with R3, Me |
| Nomenclature | MDAD | iPr₂—MDAD |
| Ligand structure | R1—N—N—R2 with Me, Me | Me—N—N—Me with Me, Me |
| Nomenclature | DMDAD | Me₂—DMDAD |
| Ligand structure | R2—N—C(R4,R5)—N—R1 with R3, R6 | Me—N—CH₂—CH₂—N—Me |
| Nomenclature | EDA | Me₂—EDA |
| Ligand structure | NacNac backbone with R1, R2, R3, R4 | NacNac with Et, Et |
| Nomenclature | NacNac | Et₂—NacNac |
| Ligand structure | pyrrole-imine with R | pyrrole-imine with Me |
| Nomenclature | PCAl | Me—PCAl |
| Ligand structure | R1—N—N—R2 (imidazol-2-ylidene) with R3, R4 | Me—N—N—Me with H, H |
| Nomenclature | NHCs (Imidazol-2-ylidenes) | Me—NHCs (1,3-dimethylimidazoline-2-ylidene) |

SUMMARY

Disclosed are titanium-tetrahydroaluminate molecules having one of the following general formulae:

(i) $Ti(AlH_4)_3—X_n$ wherein

X is selected from:

Compounds of N, P, As, Sb or Bi in oxidation state 3;

Compounds of O, S, Se or Te in oxidation state 2, including water, ethers, ketones, sulphoxides; or Molecules like carbon monoxide, benzene or other aromatic hydrocarbons, or dichloromethane; and $0 < n \leq 2$, preferably n is 1 or 2;

(ii) $Ti(AlH_4)_2L$, wherein L is selected from the group consisting of pentadienyl, cyclopentadienyl, hexadienyl, cyclohexadienyl, allyl, diimine (DAD), N-heterocyclic carbenes (NHC), amidinate, silyl-amidinate, formamidinate, dialkylethylenediamine (R1N—CH₂—

CH$_2$—NR2), dialkylaminoalkylborane (R1N—BR2-NR3), dialkylaminoalkylalane (R1N—AlR2-NR3), dialkylaminoalkylgallium (R1N—GaR2-NR3), β-acetylacetonate, β-diketonate, β-diketimine, and pyrrolecarbaldiminate; and (iii) Ti(AlH$_4$)L$_2$, wherein each L$^1$ and L$^2$ is independently selected from the group consisting of pentadienyl, cyclopentadienyl, hexadienyl, cyclohexadienyl, allyl, diimine (DAD), N-heterocyclic carbenes (NHCs), amidinate, silyl-amidinate, formamidinate, dialkylethylenediamine (R1N—CH$_2$—CH$_2$—NR2), dialkylaminoalkylborane (R1N—BR2-NR3), dialkylaminoalkylalane (R1N—AlR2-NR3), dialkylaminoalkylgallium (R1N—GaR2-NR3), β-acetylacetonate, β-diketonate, β-diketimine, and pyrrolecarbaldiminate, provided that L$^1$ and L$^2$ do not both equal non-substituted cyclopentadienyl ligands. The disclosed molecules may further include one or more of the following aspects:

one or more substitution groups on each L, L$^1$, or L$^2$ ligand selected from the group consisting of a C1-C6 linear, branched, and cyclic alkyl group;

each of the substitution groups of ligand L, L$^1$, or L$^2$ is independently selected from the group consisting of Me, Et, nPr, iPr, nBu, tBu, and iBu;

the molecule described by formula (i) being selected from the group consisting of Ti(AlH$_4$)$_3$-(methanol)$_n$, Ti(AlH$_4$)$_3$-(ethanol)$_n$, Ti(AlH$_4$)$_3$-(n-propanol)$_n$, Ti(AlH$_4$)$_3$-(i-propanol)$_n$, Ti(AlH$_4$)$_3$-(ethylene oxide)$_n$, Ti(AlH$_4$)$_3$-(dimethylether)$_n$, Ti(AlH$_4$)$_3$-(diethylether)$_n$, Ti(AlH$_4$)$_3$-(dimethoxymethane)$_n$, Ti(AlH$_4$)$_3$-(dimethoxyethane)$_n$, Ti(AlH$_4$)$_3$-(acetone)$_n$, Ti(AlH$_4$)$_3$-(THF)$_n$, Ti(AlH$_4$)$_3$-(methyl-THF)$_n$, Ti(AlH$_4$)$_3$-(benzene)$_n$, Ti(AlH$_4$)$_3$-(toluene)$_n$, Ti(AlH$_4$)$_3$-(mesytylene)$_n$, Ti(AlH$_4$)$_3$-(methoxybenzene)$_n$, Ti(AlH$_4$)$_3$-(dimethoxybenzene)$_n$, Ti(AlH$_4$)$_3$-(diglyme)$_n$, Ti(AlH$_4$)$_3$-(triglyme)$_n$, Ti(AlH$_4$)$_3$-(tetraglyme)$_n$, Ti(AlH$_4$)$_3$-(pyridine)$_n$, Ti(AlH$_4$)$_3$-(1-methylpyridine)$_n$, Ti(AlH$_4$)$_3$-(2-methylpyridine)$_n$, Ti(AlH$_4$)$_3$-(3-methylpyridine)$_n$, Ti(AlH$_4$)$_3$-(bipyridine)$_n$, Ti(AlH$_4$)$_3$-(pyridazine)$_n$, Ti(AlH$_4$)$_3$-(pyrimidine)$_n$, Ti(AlH$_4$)$_3$-(pyrazine)$_n$, Ti(AlH$_4$)$_3$-(Me$_3$N)$_n$, Ti(AlH$_4$)$_3$-(tBuMe$_2$N)$_n$, Ti(AlH$_4$)$_3$-(Et$_3$N)$_n$, Ti(AlH$_4$)$_3$-(nPr$_3$N)$_n$, Ti(AlH$_4$)$_3$-(iPr$_3$N)$_n$, Ti(AlH$_4$)$_3$-(Me$_2$NH)$_n$, Ti(AlH$_4$)$_3$-(Et$_2$NH)$_n$, Ti(AlH$_4$)$_3$-(iPr$_2$NH)$_n$, Ti(AlH$_4$)$_3$-(nPr$_2$NH)$_n$, Ti(AlH$_4$)$_3$-(MeNH$_2$)$_n$, Ti(AlH$_4$)$_3$-(EtNH$_2$)$_n$, Ti(AlH$_4$)$_3$-(nPrNH$_2$)$_n$, Ti(AlH$_4$)$_3$-(iPrNH$_2$)$_n$, Ti(AlH$_4$)$_3$-(Me$_3$P)$_n$, Ti(AlH$_4$)$_3$-(tBuMe$_2$P)$_n$, Ti(AlH$_4$)$_3$-(Et$_3$P)$_n$, Ti(AlH$_4$)$_3$-(nPr$_3$P)$_n$, Ti(AlH$_4$)$_3$-(iPr$_3$P)$_n$, Ti(AlH$_4$)$_3$-(Me$_2$PH)$_n$, Ti(AlH$_4$)$_3$-(Et$_2$PH)$_n$, Ti(AlH$_4$)$_3$-(iPr$_2$PH)$_n$, Ti(AlH$_4$)$_3$-(nPr$_2$PH)$_n$, Ti(AlH$_4$)$_3$-(MePH$_2$)$_n$, Ti(AlH$_4$)$_3$-(EtPH$_2$)$_n$, Ti(AlH$_4$)$_3$-(nPrPH$_2$)$_n$, Ti(AlH$_4$)$_3$-(iPrPH$_2$)$_n$, Ti(AlH$_4$)$_3$-(Me$_3$As)$_n$, Ti(AlH$_4$)$_3$-(tBuMe$_2$As)$_n$, Ti(AlH$_4$)$_3$-(Et$_3$As)$_n$, Ti(AlH$_4$)$_3$-(nPr$_3$As)$_n$, Ti(AlH$_4$)$_3$-(iPr$_3$As)$_n$, Ti(AlH$_4$)$_3$-(Me$_2$AsH)$_n$, Ti(AlH$_4$)$_3$-(Et$_2$AsH)$_n$, Ti(AlH$_4$)$_3$-(iPr$_2$AsH)$_n$, Ti(AlH$_4$)$_3$-(nPr$_2$AsH)$_n$, Ti(AlH$_4$)$_3$-(MeAsH$_2$)$_n$, Ti(AlH$_4$)$_3$-(EtAsH$_2$)$_n$, Ti(AlH$_4$)$_3$-(nPrAsH$_2$)$_n$, and Ti(AlH$_4$)$_3$-(iPrAsH$_2$)$_n$;

the molecule described by formula (ii) being selected from the group consisting of Ti(AlH$_4$)$_2$(H$_2$-DAD)), Ti(AlH$_4$)$_2$(Me$_2$-DAD), Ti(AlH$_4$)$_2$(Et$_2$-DAD), Ti(AlH$_4$)$_2$(iPr$_2$-DAD), Ti(AlH$_4$)$_2$(nPr$_2$-DAD), Ti(AlH$_4$)$_2$(nBu$_2$-DAD), Ti(AlH$_4$)$_2$(sBu$_2$-DAD), Ti(AlH$_4$)$_2$(iBu$_2$-DAD), Ti(AlH$_4$)$_2$(tBu$_2$-DAD), Ti(AlH$_4$)$_2$(iPr$_2$-MDAD), Ti(AlH$_4$)$_2$(Me$_2$-DMDAD), Ti(AlH$_4$)$_2$(H$_2$-fAM), Ti(AlH$_4$)$_2$(iPr$_2$-DMDAD), Ti(AlH$_4$)$_2$(Me$_2$-fAMD), Ti(AlH$_4$)$_2$(Et$_2$-fAMD), Ti(AlH$_4$)$_2$(iPr$_2$-fAMD), Ti(AlH$_4$)$_2$(nPr$_2$-fAMD), Ti(AlH$_4$)$_2$(nBu$_2$-fAMD), Ti(AlH$_4$)$_2$(iBu$_2$-fAMD), Ti(AlH$_4$)$_2$(tBu$_2$-fAMD), Ti(AlH$_4$)$_2$(sBu$_2$-fAMD), Ti(AlH$_4$)$_2$(H$_2$-AMD), Ti(AlH$_4$)$_2$(Me$_2$-AMD), Ti(AlH$_4$)$_2$(Et$_2$-AMD), Ti(AlH$_4$)$_2$(iPr$_2$-AMD), Ti(AlH$_4$)$_2$(nPr$_2$-AMD), Ti(AlH$_4$)$_2$(tBu$_2$-AMD), Ti(AlH$_4$)$_2$(nBu$_2$-AMD), Ti(AlH$_4$)$_2$(sBu$_2$-AMD), Ti(AlH$_4$)$_2$(iBu$_2$-AMD), Ti(AlH$_4$)$_2$(H$_2$—SiAMD), Ti(AlH$_4$)$_2$(Me$_2$-SiAMD), Ti(AlH$_4$)$_2$(Et$_2$-SiAMD), Ti(AlH$_4$)$_2$(iPr$_2$—SiAMD), Ti(AlH$_4$)$_2$(nPr$_2$—SiAMD), Ti(AlH$_4$)$_2$(tBu$_2$-SiAMD), Ti(AlH$_4$)$_2$(nBu$_2$-SiAMD), Ti(AlH$_4$)$_2$(sBu$_2$-SiAMD), Ti(AlH$_4$)$_2$(iBu$_2$-SiAMD), Ti(AlH$_4$)$_2$(H$_2$-NacNac), Ti(AlH$_4$)$_2$(Me$_2$-NacNac), Ti(AlH$_4$)$_2$(Et$_2$-NacNac), Ti(AlH$_4$)$_2$(iPr$_2$-NacNac), Ti(AlH$_4$)$_2$(nPr$_2$-NacNac), Ti(AlH$_4$)$_2$(tBu$_2$-NacNac), Ti(AlH$_4$)$_2$(nBu$_2$-NacNac), Ti(AlH$_4$)$_2$(sBu$_2$-NacNac), Ti(AlH$_4$)$_2$(iBu$_2$-NacNac), Ti(AlH$_4$)$_2$(H-acNac), Ti(AlH$_4$)$_2$(Me-acNac), Ti(AlH$_4$)$_2$(Et-acNac), Ti(AlH$_4$)$_2$(iPr-acNac), Ti(AlH$_4$)$_2$(nPr-acNac), Ti(AlH$_4$)$_2$(tBu-acNac), Ti(AlH$_4$)$_2$(nBu-acNac), Ti(AlH$_4$)$_2$(sBu-acNac), Ti(AlH$_4$)$_2$(iBu-acNac), Ti(AlH$_4$)$_2$(acac), Ti(AlH$_4$)$_2$Cp, Ti(AlH$_4$)$_2$(Me-Cp), Ti(AlH$_4$)$_2$(Et-Cp), Ti(AlH$_4$)$_2$(iPr-Cp), Ti(AlH$_4$)$_2$(Me$_3$-Cp), Ti(AlH$_4$)$_2$(Me$_4$-Cp), Ti(AlH$_4$)$_2$(Me$_5$-Cp), Ti(AlH$_4$)$_2$(iPr$_3$-Cp), Ti(AlH$_4$)$_2$(tBu$_3$-Cp), Ti(AlH$_4$)$_2$Op, Ti(AlH$_4$)$_2$(Me-Op), Ti(AlH$_4$)$_2$(Et-Op), Ti(AlH$_4$)$_2$(iPr-Op), Ti(AlH$_4$)$_2$(Me$_3$-Op), Ti(AlH$_4$)$_2$(Me$_4$-Op), Ti(AlH$_4$)$_2$(Me$_5$-Op), Ti(AlH$_4$)$_2$(iPr$_3$-Op), Ti(AlH$_4$)$_2$(tBu$_3$-Op), Ti(AlH$_4$)$_2$(CHDI), Ti(AlH$_4$)$_2$(Me-CHDI), Ti(AlH$_4$)$_2$(Et-CHDI), Ti(AlH$_4$)$_2$(iPr—CHDI), Ti(AlH$_4$)$_2$(Me$_3$-CHDI), Ti(AlH$_4$)$_2$(Me$_4$-CHDI), Ti(AlH$_4$)$_2$(Me$_5$-CHDI), Ti(AlH$_4$)$_2$(iPr$_3$-CHDI), Ti(AlH$_4$)$_2$(tBu$_3$-CHDI), Ti(AlH$_4$)$_2$(HDI), Ti(AlH$_4$)$_2$(Me-HDI), Ti(AlH$_4$)$_2$(Et-HDI), Ti(AlH$_4$)$_2$(iPr—HDI), Ti(AlH$_4$)$_2$(Me$_3$-HDI), Ti(AlH$_4$)$_2$(Me$_4$-HDI), Ti(AlH$_4$)$_2$(Me$_5$-HDI), Ti(AlH$_4$)$_2$(iPr$_3$-HDI), Ti(AlH$_4$)$_2$(tBu$_3$HDI), Ti(AlH$_4$)$_2$(allyl), Ti(AlH$_4$)$_2$(Me-allyl), Ti(AlH$_4$)$_2$(Et-allyl), Ti(AlH$_4$)$_2$(iPr-allyl), Ti(AlH$_4$)$_2$(Me$_2$-allyl), Ti(AlH$_4$)$_2$(Me$_3$-allyl), Ti(AlH$_4$)$_2$(Me$_2$-DAAB), Ti(AlH$_4$)$_2$(Et$_2$-DAAB), Ti(AlH$_4$)$_2$(iPr$_2$-DAAB), Ti(AlH$_4$)$_2$(nPr$_2$-DAAB), Ti(AlH$_4$)$_2$(tBu$_2$-DAAB), Ti(AlH$_4$)$_2$(nBu$_2$-DAAB), Ti(AlH$_4$)$_2$(sBu$_2$-DAAB), Ti(AlH$_4$)$_2$(iBu$_2$-DAAB), Ti(AlH$_4$)$_2$(MeEt-DAAB), Ti(AlH$_4$)$_2$(Me$_2$-DAAA), Ti(AlH$_4$)$_2$(Et$_2$-DAAA), Ti(AlH$_4$)$_2$(iPr$_2$-DAAA), Ti(AlH$_4$)$_2$(nPr$_2$-DAAA), Ti(AlH$_4$)$_2$(tBu$_2$-DAAA), Ti(AlH$_4$)$_2$(nBu$_2$-DAAA), Ti(AlH$_4$)$_2$(sBu$_2$-DAAA), Ti(AlH$_4$)$_2$(iBu$_2$-DAAA), Ti(AlH$_4$)$_2$(MeEt-DAAA), Ti(AlH$_4$)$_2$(Me$_2$-DAAG), Ti(AlH$_4$)$_2$(Et$_2$-DAAG), Ti(AlH$_4$)$_2$(iPr$_2$-DAAG), Ti(AlH$_4$)$_2$(nPr$_2$-DAAG), Ti(AlH$_4$)$_2$(tBu$_2$-DAAG), Ti(AlH$_4$)$_2$(nBu$_2$-DAAG), Ti(AlH$_4$)$_2$(sBu$_2$-DAAG), Ti(AlH$_4$)$_2$(iBu$_2$-DAAG), Ti(AlH$_4$)$_2$(MeEt-DAAG), Ti(AlH$_4$)$_2$(Me$_2$-EDA), Ti(AlH$_4$)$_2$(Et$_2$-EDA), Ti(AlH$_4$)$_2$(iPr$_2$-EDA), Ti(AlH$_4$)$_2$(nPr$_2$-EDA), Ti(AlH$_4$)$_2$(nBu$_2$-EDA), Ti(AlH$_4$)$_2$(tBu$_2$-EDA), Ti(AlH$_4$)$_2$(sBu$_2$-EDA), Ti(AlH$_4$)$_2$(iBu$_2$-EDA), Ti(AlH$_4$)$_2$(MeEt-EDA), Ti(AlH$_4$)(Me-PCAI), Ti(AlH$_4$)$_2$(Et-PCAI), Ti(AlH$_4$)$_2$(iPr-PCAI), Ti(AlH$_4$)$_2$(Me$_2$-NHCs), Ti(AlH$_4$)$_2$(Et$_2$-NHCs), Ti(AlH$_4$)$_2$(nPr$_2$—NHCs), Ti(AlH$_4$)$_2$(iPr$_2$—NHCs), Ti(AlH$_4$)$_2$(nBu$_2$-NHCs), Ti(AlH$_4$)$_2$(tBu$_2$-NHCs), Ti(AlH$_4$)$_2$(TMS$_2$—NHCs), and Ti(AlH$_4$)$_2$(Me$_2$-Me$_2$NHCs); and the molecule described by formula (iii) being selected from the group consisting of Ti(AlH$_4$)(H$_2$-DAD)$_2$, Ti(AlH$_4$)(Me$_2$-DAD)$_2$, Ti(AlH$_4$)(Et$_2$-DAD)$_2$, Ti(AlH$_4$)(iPr$_2$-DAD)$_2$, Ti(AlH$_4$)(nPr$_2$-DAD)$_2$, Ti(AlH$_4$)(nBu$_2$-DAD)$_2$, Ti(AlH$_4$)(sBu$_2$-DAD)$_2$, Ti(AlH$_4$)(iBu$_2$-DAD)$_2$, Ti(AlH$_4$)(tBu$_2$-DAD)$_2$, Ti(AlH$_4$)(Me$_2$-MDAD)$_2$, Ti(AlH$_4$)(Me$_2$-DMDAD)$_2$, Ti(AlH$_4$)(iPr$_2$-DMDAD)$_2$, Ti(AlH$_4$)(H$_2$-fAMD)$_2$, Ti(AlH$_4$)(Me$_2$-fAMD)$_2$, Ti(AlH$_4$)(Et$_2$-fAMD)$_2$, Ti(AlH$_4$)(iPr$_2$-fAMD)$_2$, Ti(AlH$_4$)(nPr$_2$-fAMD)$_2$, Ti(AlH$_4$)(nBu$_2$-fAMD)$_2$, Ti(AlH$_4$)(iBu$_2$-fAMD)$_2$, Ti(AlH$_4$)(tBu$_2$-fAMD)$_2$, Ti(AlH$_4$)(sBu$_2$-fAMD)$_2$, Ti(AlH$_4$)(H$_2$-AMD)$_2$, Ti(AlH$_4$)(Me$_2$-AMD)$_2$, Ti(AlH$_4$)(Et$_2$-AMD)$_2$, Ti(AlH$_4$)(iPr$_2$-AMD)$_2$, Ti(AlH$_4$)(nPr$_2$-AMD)$_2$, Ti(AlH$_4$)(tBu$_2$-AMD)$_2$, Ti(AlH$_4$)(nBu$_2$-AMD)$_2$, Ti(AlH$_4$)(sBu$_2$-AMD)$_2$, Ti(AlH$_4$)(iBu$_2$-AMD)$_2$, Ti(AlH$_4$)(H$_2$—SiAMD)$_2$, Ti(AlH$_4$)(Me$_2$-SiAMD)$_2$, Ti(AlH$_4$)(Et$_2$-SiAMD)$_2$, Ti(AlH$_4$)(iPr$_2$—SiAMD)$_2$, Ti(AlH$_4$)(nPr$_2$—SiAMd)$_2$, Ti(AlH$_4$)(tBu$_2$-SiAMD)$_2$, Ti(AlH$_4$)(nBu$_2$-SiAMD)$_2$, Ti(AlH$_4$)(sBu$_2$-SiAMD)$_2$, Ti(AlH$_4$)(iBu$_2$-SiAMD)$_2$, Ti(AlH$_4$)(H$_2$-NacNac)$_2$, Ti(AlH$_4$)(Me$_2$-NacNac)$_2$, Ti(AlH$_4$)(Et$_2$-NacNac)$_2$, Ti(AlH$_4$)(iPr$_2$-NacNac)$_2$, Ti(AlH$_4$)(nPr$_2$-NacNac)$_2$, Ti(AlH$_4$)(tBu$_2$-NacNac)$_2$, Ti(AlH$_4$)(nBu$_2$-NacNac)$_2$, Ti(AlH$_4$)(sBu$_2$-NacNac)$_2$, Ti(AlH$_4$)(iBu$_2$-NacNac)$_2$, Ti(AlH$_4$)(H-acNac)$_2$, Ti(AlH$_4$)(Me-acNac)$_2$, Ti(AlH$_4$)(Et-acNac)$_2$, Ti(AlH$_4$)(iPr-acNac)$_2$, Ti(AlH$_4$)(nPr-acNac)$_2$, Ti(AlH$_4$)(tBu-acNac)$_2$, Ti(AlH$_4$)(nBu-acNac)$_2$, Ti(AlH$_4$)(sBu-acNac)$_2$, Ti(AlH$_4$)(iBu-acNac)$_2$, Ti(AlH$_4$)(acac)$_2$, Ti(AlH$_4$)Cp$_2$, Ti(AlH$_4$)(Me-Cp)$_2$, Ti(AlH$_4$)(Et-Cp)$_2$, Ti(AlH$_4$)(iPr-Cp)$_2$, Ti(AlH$_4$)(Me$_3$-Cp)$_2$, Ti(AlH$_4$)(Me$_4$-Cp)$_2$, Ti(AlH$_4$)(Me$_5$-Cp)$_2$, Ti(AlH$_4$)(iPr$_3$-Cp)$_2$, Ti(AlH$_4$)(tBu$_3$-Cp)$_2$, Ti(AlH$_4$)Op$_2$, Ti(AlH$_4$)(Me-Op)$_2$, Ti(AlH$_4$)(Et-Op)$_2$, Ti(AlH$_4$)(iPr-Op)$_2$, Ti(AlH$_4$)(Me$_3$-Op)$_2$, Ti(AlH$_4$)(Me$_4$-Op)$_2$, Ti(AlH$_4$)(Me$_5$-Op)$_2$, Ti(AlH$_4$)(iPr$_3$-Op)$_2$, Ti(AlH$_4$)(tBu$_3$-Op)$_2$, Ti(AlH$_4$)(CHDI)$_2$, Ti(AlH$_4$)(Me-CHDI)$_2$, Ti(AlH$_4$)(Et-CHDI)$_2$, Ti(AlH$_4$)(iPr—CHDI)$_2$, Ti(AlH$_4$)(Me$_3$-CHDI)$_2$, Ti(AlH$_4$)(Me$_4$-CHDI)$_2$, Ti(AlH$_4$)(Me$_5$-CHDI)$_2$, Ti(AlH$_4$)(iPr$_3$-CHDI)$_2$, Ti(AlH$_4$)(tBu$_3$-CHDI)$_2$, Ti(AlH$_4$)(HDI)$_2$, Ti(AlH$_4$)(Me-HDI)$_2$, Ti(AlH$_4$)(Et-HDI)$_2$, Ti(AlH$_4$)(iPr—HDI)$_2$, Ti(AlH$_4$)(Me$_3$-HDI)$_2$, Ti(AlH$_4$)(Me$_4$-HDI)$_2$, Ti(AlH$_4$)(Me$_5$-HDI)$_2$, Ti(AlH$_4$)(iPr$_3$-HDI)$_2$, Ti(AlH$_4$)(tBu$_3$-HDI)$_2$, Ti(AlH$_4$)(allyl)$_2$, Ti(AlH$_4$)(Me-allyl)$_2$, Ti(AlH$_4$)(Et-allyl)$_2$, Ti(AlH$_4$)(iPr-allyl)$_2$, Ti(AlH$_4$)(Me$_2$-allyl)$_2$, Ti(AlH$_4$)(Me$_3$-allyl)$_2$, Ti(AlH$_4$)(Me$_2$-DAAB)$_2$, Ti(AlH$_4$)(Et$_2$-DAAB)$_2$, Ti(AlH$_4$)(iPr$_2$-DAAB)$_2$, Ti(AlH$_4$)(nPr$_2$-DAAB)$_2$, Ti(AlH$_4$)(tBu$_2$-DAAB)$_2$, Ti(AlH$_4$)(nBu$_2$-DAAB)$_2$, Ti(AlH$_4$)(sBu$_2$-DAAB)$_2$, Ti(AlH$_4$)(iBu$_2$-DAAB)$_2$, Ti(AlH$_4$)(MeEt-DAAB)$_2$, Ti(AlH$_4$)(Me$_2$-DAAA)$_2$, Ti(AlH$_4$)(Et$_2$-DAAA)$_2$, Ti(AlH$_4$)(iPr$_2$-DAAA)$_2$, Ti(AlH$_4$)(nPr$_2$-DAAA)$_2$, Ti(AlH$_4$)(tBu$_2$-DAAA)$_2$, Ti(AlH$_4$)(nBu$_2$-DAAA)$_2$, Ti(AlH$_4$)(sBu$_2$-DAAA)$_2$, Ti(AlH$_4$)(iBu$_2$-DAAA)$_2$, Ti(AlH$_4$)(MeEt-DAAA)$_2$, Ti(AlH$_4$)(Me$_2$-DAAG)$_2$, Ti(AlH$_4$)(Et$_2$-DAAG)$_2$, Ti(AlH$_4$)(iPr$_2$-DAAG)$_2$, Ti(AlH$_4$)(nPr$_2$-DAAG)$_2$, Ti(AlH$_4$)(tBu$_2$-DAAG)$_2$, Ti(AlH$_4$)(nBu$_2$-DAAG)$_2$, Ti(AlH$_4$)(sBu$_2$-DAAG)$_2$, Ti(AlH$_4$)(iBu$_2$-DAAG)$_2$, Ti(AlH$_4$)(MeEt-DAAG)$_2$, Ti(AlH$_4$)(Me$_2$-EDA)$_2$, Ti(AlH$_4$)(Et$_2$-EDA)$_2$, Ti(AlH$_4$)(iPr$_2$-EDA)$_2$, Ti(AlH$_4$)(nPr$_2$-EDA)$_2$, Ti(AlH$_4$)(nBu$_2$-EDA)$_2$, Ti(AlH$_4$)(tBu$_2$-EDA)$_2$, Ti(AlH$_4$)(sBu$_2$-EDA)$_2$, Ti(AlH$_4$)(iBu$_2$-EDA)$_2$, Ti(AlH$_4$)(MeEt-EDA)$_2$, Ti(AlH4)(Me-PCAI)$_2$, Ti(AlH4)(Et-PCAI)$_2$, Ti(AlH4)(iPr-PCAI)$_2$, Ti(AlH$_4$)(Me$_2$-NHCs)$_2$, Ti(AlH$_4$)(Et$_2$-NHCs)$_2$, Ti(AlH$_4$)(nPr$_2$—NHCs)$_2$, Ti(AlH$_4$)(iPr$_2$—NHCs)$_2$, Ti(AlH$_4$)(nBu$_2$-NHCs)$_2$, Ti(AlH$_4$)(tBu$_2$-NHCs)$_2$, Ti(AlH$_4$)(TMS$_2$—NHCs)$_2$, and Ti(AlH$_4$)(Me$_2$-Me$_2$NHCs)$_2$.

Also disclosed are methods of depositing a titanium-aluminum containing film. At least one titanium-tetrahydroaluminate precursor disclosed above is introduced into a reactor having at least one substrate disposed therein. At least part of the titanium-tetrahydroaluminate precursor is deposited onto the at least one substrate to form the titanium-aluminum containing film. The disclosed methods may further include one or more of the following aspects:

Performing the method at a temperature between about 20° C. and about 800° C., preferably between about 100° C. and about 600° C.;

performing the method at a pressure between about 0.1 Pa and about 10$^5$ Pa, preferably between about 2.5 Pa and about 10$^3$ Pa;

the deposition method being selected from the group consisting of chemical vapor deposition (CVD), atomic layer deposition (ALD), plasma CVD, plasma ALD, pulse CVD, low pressure CVD, subatmospheric CVD, and atmospheric pressure CVD;

the titanium-aluminum containing film being selected from the group consisting of pure titanium-aluminum (TiAl), titanium-aluminum nitride (TiAlN), titanium-aluminum carbide (TiAlC), titanium-aluminum carbonitride (TiAlCN), titanium-aluminum silicide ((TiAl)Si), titanium-aluminum siliconitride ((TiAl)SiN), titanium-aluminum boron ((TiAl)B), titanium-aluminum boron nitride ((TiAl)BN), titanium-aluminum oxide (TiAlO), and titanium-aluminum nitroxide (TiAlNO);

introducing a reaction gas into the reactor at the same time or at an alternate time as the introduction of the titanium-tetrahydroaluminate precursor;

depositing at least part of the titanium-tetrahydroaluminate precursor onto the at least one substrate to form the titanium-aluminum containing film by reacting the reaction gas with the titanium-tetrahydroaluminate precursor;

the reaction gas being a reducing agent;

the reducing agent being selected from the group consisting of: $N_2$, $H_2$; $SiH_4$; $Si_2H_6$; $Si_3H_8$; $NH_3$; $(CH_3)_2SiH_2$; $(C_2H_5)_2SiH_2$; $(CH_3)SiH_3$; $(C_2H_5)SiH_3$; phenyl silane; $N_2H_4$; $N(SiH_3)_3$; $N(CH_3)H_2$; $N(C_2H_5)H_2$; $N(CH_3)_2H$; $N(C_2H_5)_2H$; $N(CH_3)_3$; $N(C_2H_5)_3$; $(SiMe_3)_2NH$; $(CH_3)HNNH_2$; $(CH_3)_2NNH_2$; phenyl hydrazine; $B_2H_6$; 9-borabicyclo[3,3,1]nonane; dihydrobenzenfuran; pyrazoline; trimethylaluminum; dimethylzinc; diethylzinc; radical species thereof; and mixtures thereof;

the reaction gas being an oxidizing agent; and the oxidizing agent being selected from the group consisting of: $O_2$; $O_3$; $H_2O$; $H_2O_2$; NO; $NO_2$; carboxylic acids; radical species thereof; and mixtures thereof.

DETAILED DESCRIPTION OF PREFERRED EMBODIMENTS

Disclosed are titanium-tetrahydroaluminate bi-metallic molecules, their synthesis and their usage for the vapor deposition of TiAl-based films. The disclosed titanium-tetrahydroaluminate bi-metallic molecules may have one of the following general formulae:

$$Ti(AlH_4)_3-X_n; \quad (i)$$

$$Ti(AlH_4)_2L; \text{ or} \quad (ii)$$

$$Ti(AlH_4)L^1L^2; \quad (iii)$$

wherein
each —X is independently selected from:
compounds of N, P, As, Sb or Bi in oxidation state 3;
compounds of O, S, Se or Te in oxidation state 2, including water, ethers, ketones, sulphoxides; or molecules like carbon monoxide, benzene or other aromatic hydrocarbons, dichloromethane;

n is a number between 0 and 2 (0 excluded; in other words, 0<n≤2).

L, $L^1$, and $L^2$ is each independently selected from the group consisting of pentadienyl, cyclopentadienyl, hexadienyl, cyclohexadienyl, allyl, diimine (DAD), carbene (NHCs), amidinate, silyl-amidinate, formamidinate, dialkylethylenediamine (R1N—$CH_2$—$CH_2$—NR2), dialkylaminoalkylborane (R1N—BR2-NR3), dialkylaminoalkylalane (R1N—AlR2-NR3), dialkylaminoalkylgallium (R1N—GaR2-NR3), β-acetylacetonate, β-diketonate, β-diketimine, and pyrrolecarbaldiminate, provided that $L^1$ and $L^2$ do not both equal non-substituted cyclopentadienyl ligands.

The disclosed titanium-tetrahydroaluminate based molecules may have the following formula:

$$Ti(AlH_4)_3-X_n \quad (i)$$

wherein

Each —X is independently selected from:

Compounds of N, P, As, Sb or Bi in oxidation state 3;

Compounds of O, S, Se or Te in oxidation state 2, including water, ethers, ketones, or sulphoxides; or Molecules like carbon monoxide, benzene or other aromatic hydrocarbons, or dichloromethane; and n is a number between 0 and 2 (0 excluded; in other words, 0<n≤2). One of ordinary skill in the art will recognize that the "—" notation indicates that the X is adducted to $Ti(AlH_4)_3$.

The Lewis base —X may be selected from ethers (including cyclic ethers), ketones, alcohols, and N based compounds in oxidation state 3.

Exemplary ethers and ketones include ethylene oxide, dimethyl ether, diethyl ether, dimethoxymethane, dimethoxyethane, tetrahydrofuran, methoxybenzene, dimethoxybenzene, diglyme, triglyme, or tetraglyme.

When a cyclic ether is used, the possibility to have substitution groups (on carbon for example) is also considered. More particularly, linear or cyclic $C_1$-$C_4$ alkyl groups (examples given Me, Et, iPr, nPr, iBu, tBu, sBu, nBu), may be used as substitution groups. One example of an ether substituted with an alkyl group is 2-methyltetrahydrofuran.

When the Lewis base —X is selected from N, P, or As based compounds, it is selected from, but not limited to, pyridine, bipyridine (2,2-bipyridine or 4,4-bipyridine), pyridazine, pyrimidine, pyrazine, trialkylamine ($Me_3N$, $Et_3N$, $Pr_3N$, $tBu_3N$, $Ph_3N$, $tBuMe_2N$), dialkylamine ($Me_2NH$, $Et_2NH$, etc), alkylamine ($MeNH_2$, $EtNH_2$, etc), trialkylphosphine ($Me_3P$, $Et_3P$, $nPr_3P$, $iPr_3P$, $tBu_3P$, $Ph_3P$, $tBuMe_2P$), dialkylphosphine ($Et_2PH$, $tBu_2PH$, etc), alkylphosphine ($EtPH_2$, etc), trialkylarsine ($Me_3As$, $Et_3As$, $Pr_3As$, $Bu_3As$, $Ph_3As$, $tBuMe_2As$), dialkylarsine ($Et_2AsH$, $HBu_2AsH$, etc), or alkylarsine ($EtAsH_2$, etc).

When a cyclic Lewis base is selected from N, P, or As based compounds, the possibility to have substitution groups (on carbon for example) is also considered. More particularly, linear or cyclic $C_1$-$C_4$ alkyl groups (examples given Me, Et, iPr, nPr, iBu, tBu, sBu, nBu), may be used as substitution groups. Some exemplary Lewis bases substituted with an alkyl group include 2-methylpyridine, 3-methylpyridine, and 4-methylpyridine.

n is a number between 0 and 2 (0 excluded, in other words 0<n≤2). In a preferred embodiment, n is 1 or 2.

The titanium-tetrahydroaluminate precursor having the formula (i), for instance $Ti(AlH_4)_3$(dme), may be synthesized as described in Example 1.

Exemplary titanium-tetrahydroaluminate bi-metallic containing precursors of formula (i) include, without limitation $Ti(AlH_4)_3$-(methanol)$_n$, $Ti(AlH_4)_3$-(ethanol)$_n$, $Ti(AlH_4)_3$-(n-propanol)$_n$, $Ti(AlH_4)_3$-(i-propanol)$_n$, $Ti(AlH_4)_3$-(ethylene oxide)$_n$, $Ti(AlH_4)_3$-(dimethylether)$_n$, $Ti(AlH_4)_3$-(diethylether)$_n$, $Ti(AlH_4)_3$-(dimethoxymethane)$_n$, $Ti(AlH_4)_3$-(dimethoxyethane)$_n$, $Ti(AlH_4)_3$-(acetone)$_n$, $Ti(AlH_4)_3$-(THF)$_n$, $Ti(AlH_4)_3$-(methyl-THF)$_n$, $Ti(AlH_4)_3$-(benzene)$_n$, $Ti(AlH_4)_3$-(toluene)$_n$, $Ti(AlH_4)_3$-(mesytylene)$_n$, $Ti(AlH_4)_3$-(methoxybenzene)$_n$, $Ti(AlH_4)_3$-(dimethoxybenzene)$_n$, $Ti(AlH_4)_3$-(diglyme)$_n$, $Ti(AlH_4)_3$-(triglyme)$_n$, $Ti(AlH_4)_3$-(tetraglyme)$_n$, $Ti(AlH_4)_3$-(pyridine)$_n$, $Ti(AlH_4)_3$-(1-methylpyridine)$_n$, $Ti(AlH_4)_3$-(2-methylpyridine)$_n$, $Ti(AlH_4)_3$-(3-methylpyridine)$_n$, $Ti(AlH4)_3$-(bipyridine)$_n$, $Ti(AlH_4)_3$-(pyridazine)$_n$, $Ti(AlH_4)_3$-(pyrimidine)$_n$, $Ti(AlH_4)_3$-(pyrazine)$_n$, $Ti(AlH_4)_3$-($Me_3N$)$_n$, $Ti(AlH_4)_3$-($tBuMe_2N$)$_n$, $Ti(AlH_4)_3$-($Et_3N$)$_n$, $Ti(AlH_4)_3$-($nPr_3N$)$_n$, $Ti(AlH_4)_3$-($iPr_3N$)$_n$, $Ti(AlH_4)_3$-($Me_2NH$)$_n$, $Ti(AlH_4)_3$-($Et_2NH$)$_n$, $Ti(AlH_4)_3$-($iPr_2NH$)$_n$, $Ti(AlH_4)_3$-($nPr_2NH$)$_n$, $Ti(AlH_4)_3$-($MeNH_2$)$_n$, $Ti(AlH_4)_3$-($EtNH_2$)$_n$, $Ti(AlH_4)_3$-($nPrNH_2$)$_n$, $Ti(AlH_4)_3$-($iPrNH_2$)$_n$, $Ti(AlH_4)_3$-($Me_3P$)$_n$, $Ti(AlH_4)_3$-($tBuMe_2P$)$_n$, $Ti(AlH_4)_3$-($Et_3P$)$_n$, $Ti(AlH_4)_3$-($nPr_3P$)$_n$, $Ti(AlH_4)_3$-($iPr_3P$)$_n$, $Ti(AlH_4)_3$-($Me_2PH$)$_n$, $Ti(AlH_4)_3$-($Et_2PH$)$_n$, $Ti(AlH_4)_3$-($iPr_2PH$)$_n$, $Ti(AlH_4)_3$-($nPr_2PH$)$_n$, $Ti(AlH_4)_3$-($MePH_2$)$_n$, $Ti(AlH_4)_3$-($EtPH_2$)$_n$, $Ti(AlH_4)_3$-($nPrPH_2$)$_n$, $Ti(AlH_4)_3$-($iPrPH_2$)$_n$, $Ti(AlH_4)_3$-($Me_3As$)$_n$, $Ti(AlH_4)_3$-($tBuMe_2As$)$_n$, $Ti(AlH_4)_3$-($Et_3As$)$_n$, $Ti(AlH_4)_3$-($nPr_3As$)$_n$, $Ti(AlH_4)_3$-($iPr_3As$)$_n$, $Ti(AlH_4)_3$-($Me_2AsH$)$_n$, $Ti(AlH_4)_3$-($Et_2AsH$)$_n$, $Ti(AlH_4)_3$-($iPr_2AsH$)$_n$, $Ti(AlH_4)_3$-($nPr_2AsH$)$_n$, $Ti(AlH_4)_3$-($MeAsH_2$)$_n$, $Ti(AlH_4)_3$-($EtAsH_2$)$_n$, $Ti(AlH_4)_3$-($nPrAsH_2$)$_n$, or $Ti(AlH_4)_3$-($iPrAsH_2$)$_n$. Preferably, the titanium-tetrahydroaluminate precursor having the formula (i) is $Ti(AlH_4)_3$(dimethoxyethane), $Ti(AlH_4)_3$(pyridine), or $Ti(AlH_4)_3$(THF).

The disclosed titanium-tetrahydroaluminate based molecules may have the following formulae:

$$Ti(AlH_4)_2L, \quad (ii)$$

having the structural formula:

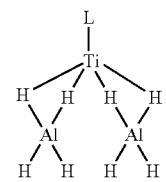

wherein L is selected from the group consisting of pentadienyl, cyclopentadienyl, hexadienyl, cyclohexadienyl, allyl, diimine (DAD), carbene (NHCs), amidinate, silyl-amidinate, formamidinate, dialkylethylenediamine (R1N—$CH_2$—$CH_2$—NR2), dialkylaminoalkylborane (R1N—BR2-NR3), dialkylaminoalkylalane (R1N—AlR2-NR3), dialkylaminoalkylgallium (R1N—GaR2-NR3), β-acetylacetonate, β-diketonate, β-diketimine, and pyrrolecarbaldiminate.

The L ligand may be substituted, meaning that any hydrogen (H) atom linked to any of the O, C, or N atom present in the backbone structure of the ligand may instead be a C1-C6 linear, branched, or cyclic alkyl group; a C1-C6 linear, branched, or cyclic alkylsilyl group (mono, bis, or tris alkyl); a C1-C6 linear, branched, or cyclic alkylamino group such as NRR', where R and R' are independently selected from H or C1-C6 linear, branched, or cyclic alkyl or aryl group; and a C1-C6 linear, branched, or cyclic fluoroalkyl group in which some or all of the substituents are F (i.e. partially or totally fluorinated alkyl group). Preferably such substitution groups are independently selected from H or a C1-C6 linear, branched, or cyclic alkyl group. Preferably such substitution groups are independently selected from the group consisting of Me, Et, nPr, iPr, nBu, tBu, sBu, and iBu.

The titanium-tetrahydroaluminate precursor having the formula (ii), for instance Ti(AlH$_4$)$_2$(iPr-DAD), may be synthesized as described in example 2.

Exemplary titanium-tetrahydroaluminate containing precursors of formula (ii) include without limitation Ti(AlH$_4$)$_2$ (H$_2$-DAD)), Ti(AlH$_4$)$_2$(Me$_2$-DAD), Ti(AlH$_4$)$_2$(Et$_2$-DAD), Ti(AlH$_4$)$_2$(iPr$_2$-DAD), Ti(AlH$_4$)$_2$(nPr$_2$-DAD), Ti(AlH$_4$)$_2$(nBu$_2$-DAD), Ti(AlH$_4$)$_2$(sBu$_2$-DAD), Ti(AlH$_4$)$_2$(iBu$_2$-DAD), Ti(AlH$_4$)$_2$(tBu$_2$-DAD), Ti(AlH$_4$)$_2$(iPr$_2$-MDAD), Ti(AlH$_4$)$_2$(Me$_2$-DMDAD), Ti(AlH$_4$)$_2$(iPr$_2$-DMDAD), Ti(AlH$_4$)$_2$(H$_2$-fAM), Ti(AlH$_4$)$_2$(Me$_2$-fAMD), Ti(AlH$_4$)$_2$(Et$_2$-fAMD), Ti(AlH$_4$)$_2$(iPr$_2$-fAMD), Ti(AlH$_4$)$_2$(nPr$_2$-fAMD), Ti(AlH$_4$)$_2$(nBu$_2$-fAMD), Ti(AlH$_4$)$_2$(iBu$_2$-fAMD), Ti(AlH$_4$)$_2$(tBu$_2$-fAMD), Ti(AlH$_4$)$_2$(sBu$_2$-fAMD), Ti(AlH$_4$)$_2$(H$_2$-AMD), Ti(AlH$_4$)$_2$(Me$_2$-AMD), Ti(AlH$_4$)$_2$(Et$_2$-AMD), Ti(AlH$_4$)$_2$(iPr$_2$-AMD), Ti(AlH$_4$)$_2$(nPr$_2$-AMD), Ti(AlH$_4$)$_2$(tBu$_2$-AMD), Ti(AlH$_4$)$_2$(nBu$_2$-AMD), Ti(AlH$_4$)$_2$(sBu$_2$-AMD), Ti(AlH$_4$)$_2$(iBu$_2$-AMD), Ti(AlH$_4$)$_2$(H$_2$—SiAMD), Ti(AlH$_4$)$_2$(Me$_2$-SiAMD), Ti(AlH$_4$)$_2$(Et$_2$-SiAMD), Ti(AlH$_4$)$_2$(iPr$_2$—SiAMD), Ti(AlH$_4$)$_2$(nPr$_2$-SiAMD), Ti(AlH$_4$)$_2$(tBu$_2$-SiAMD), Ti(AlH$_4$)$_2$(nBu$_2$-SiAMD), Ti(AlH$_4$)$_2$(sBu$_2$-SiAMD), Ti(AlH$_4$)$_2$(iBu$_2$-SiAMD), Ti(AlH$_4$)$_2$(H$_2$-NacNac), Ti(AlH$_4$)$_2$(Me$_2$-NacNac), Ti(AlH$_4$)$_2$(Et$_2$-NacNac), Ti(AlH$_4$)$_2$(iPr$_2$-NacNac), Ti(AlH$_4$)$_2$(nPr$_2$-NacNac), Ti(AlH$_4$)$_2$(tBu$_2$-NacNac), Ti(AlH$_4$)$_2$(nBu$_2$-NacNac), Ti(AlH$_4$)$_2$(sBu$_2$-NacNac), Ti(AlH$_4$)$_2$(iBu$_2$-NacNac), Ti(AlH$_4$)$_2$(H-acNac), Ti(AlH$_4$)$_2$(Me-acNac), Ti(AlH$_4$)$_2$(Et-acNac), Ti(AlH$_4$)$_2$(iPr-acNac), Ti(AlH$_4$)$_2$(nPr-acNac), Ti(AlH$_4$)$_2$(tBu-acNac), Ti(AlH$_4$)$_2$(nBu-acNac), Ti(AlH$_4$)$_2$(sBu-acNac), Ti(AlH$_4$)$_2$(iBu-acNac), Ti(AlH$_4$)$_2$(acac), Ti(AlH$_4$)$_2$Cp, Ti(AlH$_4$)$_2$(Me-Cp), Ti(AlH$_4$)$_2$(Et-Cp), Ti(AlH$_4$)$_2$(iPr-Cp), Ti(AlH$_4$)$_2$(Me$_3$-Cp), Ti(AlH$_4$)$_2$(Me$_4$-Cp), Ti(AlH$_4$)$_2$(Me$_5$-Cp), Ti(AlH$_4$)$_2$(iPr$_3$-Cp), Ti(AlH$_4$)$_2$(tBu$_3$-Cp), Ti(AlH$_4$)$_2$Op, Ti(AlH$_4$)$_2$(Me-Op), Ti(AlH$_4$)$_2$(Et-Op), Ti(AlH$_4$)$_2$(iPr-Op), Ti(AlH$_4$)$_2$(Me$_3$-Op), Ti(AlH$_4$)$_2$(Me$_4$-Op), Ti(AlH$_4$)$_2$(Me$_5$-Op), Ti(AlH$_4$)$_2$(iPr$_3$-Op), Ti(AlH$_4$)$_2$(tBu$_3$-Op), Ti(AlH$_4$)$_2$(CHDI), Ti(AlH$_4$)$_2$(Me-CHDI), Ti(AlH$_4$)$_2$(Et-CHDI), Ti(AlH$_4$)$_2$(iPr—CHDI), Ti(AlH$_4$)$_2$(Me$_3$-CHDI), Ti(AlH$_4$)$_2$(Me$_4$-CHDI), Ti(AlH$_4$)$_2$(Me$_5$-CHDI), Ti(AlH$_4$)$_2$(iPr$_3$-CHDI), Ti(AlH$_4$)$_2$(tBu$_3$-CHDI), Ti(AlH$_4$)$_2$(HDI), Ti(AlH$_4$)$_2$(Me-HDI), Ti(AlH$_4$)$_2$(Et-HDI), Ti(AlH$_4$)$_2$(iPr—HDI), Ti(AlH$_4$)$_2$(Me$_3$-HDI), Ti(AlH$_4$)$_2$(Me$_4$-HDI), Ti(AlH$_4$)$_2$(Me$_5$-HDI), Ti(AlH$_4$)$_2$(iPr$_3$-HDI), Ti(AlH$_4$)$_2$(tBu$_3$HDI), Ti(AlH$_4$)$_2$(allyl), Ti(AlH$_4$)$_2$(Me-allyl), Ti(AlH$_4$)$_2$(Et-allyl), Ti(AlH$_4$)$_2$(iPr-allyl), Ti(AlH$_4$)$_2$(Me$_2$-allyl), Ti(AlH$_4$)$_2$(Me$_3$-allyl), Ti(AlH$_4$)$_2$(Me$_2$-DAAB), Ti(AlH$_4$)$_2$(Et$_2$-DAAB), Ti(AlH$_4$)$_2$(iPr$_2$-DAAB), Ti(AlH$_4$)$_2$(nPr$_2$-DAAB), Ti(AlH$_4$)$_2$(tBu$_2$-DAAB), Ti(AlH$_4$)$_2$(nBu$_2$-DAAB), Ti(AlH$_4$)$_2$(sBu$_2$-DAAB), Ti(AlH$_4$)$_2$(iBu$_2$-DAAB), Ti(AlH$_4$)$_2$(MeEt-DAAB), Ti(AlH$_4$)$_2$(Me$_2$-DAAA), Ti(AlH$_4$)$_2$(Et$_2$-DAAA), Ti(AlH$_4$)$_2$(iPr$_2$-DAAA), Ti(AlH$_4$)$_2$(nPr$_2$-DAAA), Ti(AlH$_4$)$_2$(tBu$_2$-DAAA), Ti(AlH$_4$)$_2$(nBu$_2$-DAAA), Ti(AlH$_4$)$_2$(sBu$_2$-DAAA), Ti(AlH$_4$)$_2$(iBu$_2$-DAAA), Ti(AlH$_4$)$_2$(MeEt-DAAA), Ti(AlH$_4$)$_2$(Me$_2$-DAAG), Ti(AlH$_4$)$_2$(Et$_2$-DAAG), Ti(AlH$_4$)$_2$(iPr$_2$-DAAG), Ti(AlH$_4$)$_2$(nPr$_2$-DAAG), Ti(AlH$_4$)$_2$(tBu$_2$-DAAG), Ti(AlH$_4$)$_2$(nBu$_2$-DAAG), Ti(AlH$_4$)$_2$(sBu$_2$-DAAG), Ti(AlH$_4$)$_2$(iBu$_2$-DAAG), Ti(AlH$_4$)$_2$(MeEt-DAAG), Ti(AlH$_4$)$_2$(Me$_2$-EDA), Ti(AlH$_4$)$_2$(Et$_2$-EDA), Ti(AlH$_4$)$_2$(iPr$_2$-EDA), Ti(AlH$_4$)$_2$(nPr$_2$-EDA), Ti(AlH$_4$)$_2$(nBu$_2$-EDA), Ti(AlH$_4$)$_2$(tBu$_2$-EDA), Ti(AlH$_4$)$_2$(sBu$_2$-EDA), Ti(AlH$_4$)$_2$(iBu$_2$-EDA), Ti(AlH$_4$)$_2$(MeEt-EDA), Ti(AlH$_4$)$_2$(Me-PCAI), Ti(AlH$_4$)$_2$(Et-PCAI), Ti(AlH$_4$)$_2$(iPr-PCAI), Ti(AlH$_4$)$_2$(Me$_2$-NHCs), Ti(AlH$_4$)$_2$(Et$_2$-NHCs), Ti(AlH$_4$)$_2$(nPr$_2$—NHCs), Ti(AlH$_4$)$_2$(iPr$_2$—NHCs), Ti(AlH$_4$)$_2$(nBu$_2$-NHCs), Ti(AlH$_4$)$_2$(tBu$_2$-NHCs), Ti(AlH$_4$)$_2$(TMS$_2$—NHCs), or Ti(AlH$_4$)$_2$(Me$_2$-Me$_2$NHCs).

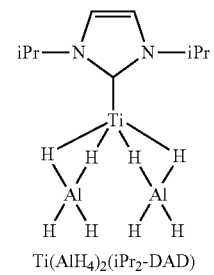

Ti(AlH$_4$)$_2$(iPr$_2$-DAD)

Preferably, the titanium-tetrahydroaluminate precursor having the formula (ii) is Ti(AlH$_4$)$_2$(iPr$_2$-DAD), Ti(AlH$_4$)$_2$(iPr$_2$-AMD), or Ti(AlH$_4$)$_2$(iPr$_2$-DAAA).

The disclosed titanium-tetrahydroaluminate based molecules may have the following formula:

$$Ti(AlH_4)L^1L^2, \quad \text{(iii)}$$

having the structural formula:

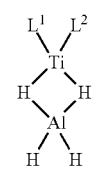

wherein each of L$^1$ and L$^2$ is independently selected from the group consisting of pentadienyl, cyclopentadienyl, hexadienyl, cyclohexadienyl, allyl, diimine (DAD), carbene (NHCs), amidinate, silyl-amidinate, formamidinate, dialkyl-ethylenediamine (R1N—CH$_2$—CH$_2$—NR2), dialkylaminoalkylborane (R1N—BR2-NR3), dialkylaminoalkylalane (R1N—AlR2-NR3), dialkylaminoalkylgallium (R1N—GaR2-NR3), β-acetylacetonate, β-diketonate, β-diketimine, and pyrrolecarbaldiminate, provided that L$^1$ and L$^2$ do not both equal non-substituted cyclopentadienyl ligands.

Each of L$^1$ and L$^2$ ligands may be substituted, meaning that any hydrogen (H) atom linked to any of the O, C, or N atom present in the backbone structure of the ligand may instead be a C1-C6 linear, branched, or cyclic alkyl group; a C1-C6 linear, branched, or cyclic alkylsilyl group (mono, bis, or tris alkyl); a C1-C6 linear, branched, or cyclic alkylamino group such as NRR', where R and R' are independently selected from H or C1-C6 linear, branched, or cyclic alkyl or aryl group; and a C1-C6 linear, branched, or cyclic fluoroalkyl group in which some or all of the substituents are F (i.e. partially or totally fluorinated alkyl group). Preferably such substitution groups are independently selected from H or a C1-C6 linear, branched, or cyclic alkyl group. Preferably such substitution groups are independently selected from the group consisting of Me, Et, nPr, iPr, nBu, tBu, sBu, and iBu.

The bi-metallic titanium-aluminum-containing precursor of formula (iii), for instance Ti(AlH$_4$)(iPr-DAD)$_2$ may be synthesized by as described in Example 3

Exemplary bi-metallic titanium-tetrahydroaluminate-containing precursors of formula (iii) include, without limitation Ti(AlH$_4$)(H$_2$-DAD)$_2$, Ti(AlH$_4$)(Me$_2$-DAD)$_2$, Ti(AlH$_4$)(Et$_2$-DAD)$_2$, Ti(AlH$_4$)(iPr$_2$-DAD)$_2$, Ti(AlH$_4$)(nPr$_2$-DAD)$_2$, Ti(AlH$_4$)(nBu$_2$-DAD)$_2$, Ti(AlH$_4$)(sBu$_2$-DAD)$_2$, Ti(AlH$_4$)(iBu$_2$-DAD)$_2$, Ti(AlH$_4$)(tBu$_2$-DAD)$_2$, Ti(AlH$_4$)(iPr$_2$-MDAD)$_2$, Ti(AlH$_4$)(Me$_2$-DMDAD)$_2$, Ti(AlH$_4$)(iPr$_2$-DMDAD)$_2$, Ti(AlH$_4$)(H$_2$-fAMD)$_2$, Ti(AlH$_4$)(Me$_2$-fAMD)$_2$, Ti(AlH$_4$)(Et$_2$-fAMD)$_2$, Ti(AlH$_4$)(iPr$_2$-fAMD)$_2$, Ti(AlH$_4$)(nPr$_2$-fAMD)$_2$, Ti(AlH$_4$)(nBu$_2$-fAMD)$_2$, Ti(AlH$_4$)(iBu$_2$-fAMD)$_2$, Ti(AlH$_4$)(tBu$_2$-fAMD)$_2$, Ti(AlH$_4$)(sBu$_2$-fAMD)$_2$, Ti(AlH$_4$)(H$_2$-AMD)$_2$, Ti(AlH$_4$)(Me$_2$-AMD)$_2$, Ti(AlH$_4$)(Et$_2$-AMD)$_2$, Ti(AlH$_4$)(iPr$_2$-AMD)$_2$, Ti(AlH$_4$)(nPr$_2$-AMd)$_2$, Ti(AlH$_4$)(tBu$_2$-AMD)$_2$, Ti(AlH$_4$)(nBu$_2$-AMD)$_2$, Ti(AlH$_4$)(sBu$_2$-AMD)$_2$, Ti(AlH$_4$)(iBu$_2$-AMD)$_2$, Ti(AlH$_4$)(H$_2$—SiAMD)$_2$, Ti(AlH$_4$)(Me$_2$-SIAMD)$_2$, Ti(AlH$_4$)(Et$_2$-SiAMD)$_2$, Ti(AlH$_4$)(iPr$_2$—SiAMD)$_2$, Ti(AlH$_4$)(nPr$_2$—SiAMd)$_2$, Ti(AlH$_4$)(tBu$_2$-SiAMD)$_2$, Ti(AlH$_4$)(nBu$_2$-SiAMD)$_2$, Ti(AlH$_4$)(sBu$_2$-SiAMD)$_2$, Ti(AlH$_4$)(iBu$_2$-SiAMD)$_2$, Ti(AlH$_4$)(H$_2$-NacNac)$_2$, Ti(AlH$_4$)(Me$_2$-NacNac)$_2$, Ti(AlH$_4$)(Et$_2$-NacNac)$_2$, Ti(AlH$_4$)(iPr$_2$-NacNac)$_2$, Ti(AlH$_4$)(nPr$_2$-NacNac)$_2$, Ti(AlH$_4$)(tBu$_2$-NacNac)$_2$, Ti(AlH$_4$)(nBu$_2$-NacNac)$_2$, Ti(AlH$_4$)(sBu$_2$-NacNac)$_2$, Ti(AlH$_4$)(iBu$_2$-NacNac)$_2$, Ti(AlH$_4$)(H-acNac)$_2$, Ti(AlH$_4$)(Me-acNac)$_2$, Ti(AlH$_4$)(Et-acNac)$_2$, Ti(AlH$_4$)(iPr-acNac)$_2$, Ti(AlH$_4$)(nPr-acNac)$_2$, Ti(AlH$_4$)(tBu-acNac)$_2$, Ti(AlH$_4$)(nBu-acNac)$_2$, Ti(AlH$_4$)(sBu-acNac)$_2$, Ti(AlH$_4$)(iBu-acNac)$_2$, Ti(AlH$_4$)(acac)$_2$, Ti(AlH$_4$)Cp$_2$, Ti(AlH$_4$)(Me-Cp)$_2$, Ti(AlH$_4$)(Et-Cp)$_2$, Ti(AlH$_4$)(iPr-Cp)$_2$, Ti(AlH$_4$)(Me$_3$-Cp)$_2$, Ti(AlH$_4$)(Me$_4$-Cp)$_2$, Ti(AlH$_4$)(Me$_5$-Cp)$_2$, Ti(AlH$_4$)(iPr$_3$-Cp)$_2$, Ti(AlH$_4$)(tBu$_3$-Cp)$_2$, Ti(AlH$_4$)Op$_2$, Ti(AlH$_4$)(Me-Op)$_2$, Ti(AlH$_4$)(Et-Op)$_2$, Ti(AlH$_4$)(iPr-Op)$_2$, Ti(AlH$_4$)(Me$_3$-Op)$_2$, Ti(AlH$_4$)(Me$_4$-Op)$_2$, Ti(AlH$_4$)(Me$_5$-Op)$_2$, Ti(AlH$_4$)(iPr$_3$-Op)$_2$, Ti(AlH$_4$)(tBu$_3$-Op)$_2$, Ti(AlH$_4$)(CHDI)$_2$, Ti(AlH$_4$)(Me-CHDI)$_2$, Ti(AlH$_4$)(Et-CHDI)$_2$, Ti(AlH$_4$)(iPr—CHDI)$_2$, Ti(AlH$_4$)(Me$_3$-CHDI)$_2$, Ti(AlH$_4$)(Me$_4$-CHDI)$_2$, Ti(AlH$_4$)(Me$_5$-CHDI)$_2$, Ti(AlH$_4$)(iPr$_3$-CHDI)$_2$, Ti(AlH$_4$)(tBu$_3$-CHDI)$_2$, Ti(AlH$_4$)(HDI)$_2$, Ti(AlH$_4$)(Me-HDI)$_2$, Ti(AlH$_4$)(Et-HDI)$_2$, Ti(AlH$_4$)(iPr—HDI)$_2$, Ti(AlH$_4$)(Me$_3$-HDI)$_2$, Ti(AlH$_4$)(Me$_4$-HDI)$_2$, Ti(AlH$_4$)(Me$_5$-HDI)$_2$, Ti(AlH$_4$)(iPr$_3$-HDI)$_2$, Ti(AlH$_4$)(tBu$_3$-HDI)$_2$, Ti(AlH$_4$)(allyl)$_2$, Ti(AlH$_4$)(Me-allyl)$_2$, Ti(AlH$_4$)(Et-allyl)$_2$, Ti(AlH$_4$)(iPr-allyl)$_2$, Ti(AlH$_4$)(Me$_2$-allyl)$_2$, Ti(AlH$_4$)(Me$_3$-allyl)$_2$, Ti(AlH$_4$)(Me$_2$-DAAB)$_2$, Ti(AlH$_4$)(Et$_2$-DAAB)$_2$, Ti(AlH$_4$)(iPr$_2$-DAAB)$_2$, Ti(AlH$_4$)(nPr$_2$-DAAB)$_2$, Ti(AlH$_4$)(tBu$_2$-DAAB)$_2$, Ti(AlH$_4$)(nBu$_2$-DAAB)$_2$, Ti(AlH$_4$)(sBu$_2$-DAAB)$_2$, Ti(AlH$_4$)(iBu$_2$-DAAB)$_2$, Ti(AlH$_4$)(MeEt-DAAB)$_2$, Ti(AlH$_4$)(Me$_2$-DAAA)$_2$, Ti(AlH$_4$)(Et$_2$-DAAA)$_2$, Ti(AlH$_4$)(iPr$_2$-DAAA)$_2$, Ti(AlH$_4$)(nPr$_2$-DAAA)$_2$, Ti(AlH$_4$)(tBu$_2$-DAAA)$_2$, Ti(AlH$_4$)(nBu$_2$-DAAA)$_2$, Ti(AlH$_4$)(sBu$_2$-DAAA)$_2$, Ti(AlH$_4$)(iBu$_2$-DAAA)$_2$, Ti(AlH$_4$)(MeEt-DAAA)$_2$, Ti(AlH$_4$)(Me$_2$-DAAG)$_2$, Ti(AlH$_4$)(Et$_2$-DAAG)$_2$, Ti(AlH$_4$)(iPr$_2$-DAAG)$_2$, Ti(AlH$_4$)(nPr$_2$-DAAG)$_2$, Ti(AlH$_4$)(tBu$_2$-DAAG)$_2$, Ti(AlH$_4$)(nBu$_2$-DAAG)$_2$, Ti(AlH$_4$)(sBu$_2$-DAAG)$_2$, Ti(AlH$_4$)(iBu$_2$-DAAG)$_2$, Ti(AlH$_4$)(MeEt-DAAG)$_2$, Ti(AlH$_4$)(Me$_2$-EDA)$_2$, Ti(AlH$_4$)(Et$_2$-EDA)$_2$, Ti(AlH$_4$)(iPr$_2$-EDA)$_2$, Ti(AlH$_4$)(nPr$_2$-EDA)$_2$, Ti(AlH$_4$)(nBu$_2$-EDA)$_2$, Ti(AlH$_4$)(tBu$_2$-EDA)$_2$, Ti(AlH$_4$)(sBu$_2$-EDA)$_2$, Ti(AlH$_4$)(iBu$_2$-EDA)$_2$, Ti(AlH$_4$)(MeEt-EDA)$_2$, Ti(AlH4)(Me-PCAI)$_2$, Ti(AlH4)(Et-PCAI)$_2$, Ti(AlH4)(iPr-PCAI)$_2$, Ti(AlH$_4$)(Me$_2$-NHCs)$_2$, Ti(AlH$_4$)(Et$_2$-NHCs)$_2$, Ti(AlH$_4$)(nPr$_2$—NHCs)$_2$, Ti(AlH$_4$)(iPr$_2$—NHCs)$_2$, Ti(AlH$_4$)(nBu$_2$-NHCs)$_2$, Ti(AlH$_4$)(tBu$_2$-NHCs)$_2$, Ti(AlH$_4$)(TMS$_2$—NHCs)$_2$, or Ti(AlH$_4$)(Me$_2$-Me$_2$NHCs)$_2$.

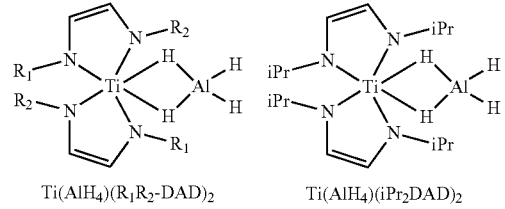

Ti(AlH$_4$)(R$_1$R$_2$-DAD)$_2$      Ti(AlH$_4$)(iPr$_2$DAD)$_2$

Preferably the bi-metallic titanium-aluminum-containing precursor of formula (iii) is Ti(AlH$_4$)(iPr-DAD)$_2$, Ti(AlH$_4$)(iPr-AMD)$_2$, or Ti(AlH$_4$)(allyl)$_2$.

The physical and thermal properties of any of the disclosed precursors vary depending upon the R substituents utilized and the oxidation state of the titanium-tetrahydroaluminate bi-metallic molecule, which allows for the development of precursors having a broad range of properties.

For instance, the variety of DAD, NHC, AMD, f-AMD, DAAB, DAAA, and DAAG ligand selections for the disclosed precursors provides the ability to synthesize a large number of precursors having different properties based on the substitution group linked to the nitrogen atom(s) present in these ligands. The variety may also provide the ability to tune the oxidation state of the titanium-tetrahydroaluminuate precursor depending on the needs and chemical-wise possibilities.

Preferably the bi-metallic titanium-tetrahydroaluminate-containing precursor is Ti(AlH$_4$)$_3$-dimethoxyether, Ti(AlH$_4$)$_2$(iPr$_2$-DAD), Ti(AlH$_4$)(iPr$_2$-DAD)$_2$, Ti(AlH$_4$)$_2$(allyl), Ti(AlH$_4$)$_2$(iPr$_2$-AMD), or Ti(AlH$_4$)$_2$(iPr$_2$-DAAA).

Also disclosed are methods for forming a titanium-aluminum-containing layer on a substrate using a vapor deposition process. The method may be useful in the manufacture of semiconductor, photovoltaic, LCD-TFT, flat panel, or MEMS type devices.

The titanium-aluminum-containing film may be deposited by introducing at least one of the disclosed bi-metallic titanium-tetrahydroaluminate precursors discussed above into a reactor having at least one substrate disposed therein. At least part of the disclosed titanium-tetrahydroaluminate precursor is deposited onto the at least one substrate to form the titanium-aluminum containing film.

The disclosed bi-metallic titanium-tetrahydroaluminate precursors may be used to deposit thin titanium-aluminum-containing films using any deposition methods known to those of skill in the art. Examples of suitable deposition methods include without limitation, conventional chemical vapor deposition (CVD) or atomic layer deposition (ALD), or other types of deposition that are related to vapor coating, using techniques such as plasma [plasma enhanced chemical vapor deposition (PECVD) or plasma enhanced atomic layer deposition (PEALD)], tuned introduction schemes [pulsed chemical vapor deposition (PCVD)], tuned reaction pressure [low pressure chemical vapor deposition (LPCVD), subatmospheric CVD (SACVD), or atmospheric pressure CVD (APCVD)], or combinations thereof. In one alternative, a thermal CVD deposition is preferred, particularly when fast growth, conformality, process-orientation and one direction films are required. In another alternative, a thermal ALD deposition process is preferred, particularly when superior conformality of films deposited on challenging surfaces (e.g., trenches, holes, vias) is required.

The disclosed titanium-tetrahydroaluminate precursors may be supplied either in neat form or in a blend with a suitable solvent, such as ethyl benzene, xylene, mesitylene, decane, dodecane. The disclosed precursors may be present in varying concentrations in the solvent.

One or more of the neat or blended titanium-tetrahydroaluminate precursors are introduced into a reactor in vapor form by conventional means, such as tubing and/or flow meters. The precursor in vapor form may be produced by vaporizing the neat or blended precursor solution through a conventional vaporization step such as direct vaporization, distillation, by bubbling, or by using a sublimator such as the one disclosed in PCT Publication WO2009/087609 to Xu et al. The neat or blended precursor may be fed in liquid state to a vaporizer where it is vaporized before it is introduced into the reactor. Alternatively, the neat or blended precursor may be vaporized by passing a carrier gas into a container containing the precursor or by bubbling the carrier gas into the precursor. The carrier gas may include, but is not limited to, Ar, He, or $N_2$, and mixtures thereof. Bubbling with a carrier gas may also remove any dissolved oxygen present in the neat or blended precursor solution. The carrier gas and precursor are then introduced into the reactor as a vapor.

If necessary, the container of disclosed precursor may be heated to a temperature that permits the precursor to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of precursor vaporized.

The reactor may be any enclosure or chamber within a device in which deposition methods take place such as, without limitation, a parallel-plate type reactor, a cold-wall type reactor, a hot-wall type reactor, a single-wafer reactor, a multi-wafers reactor, or other types of deposition systems under conditions suitable to cause the precursors to react and form the layers.

Generally, the reactor contains one or more substrates onto which the thin films will be deposited. The one or more substrates may be any suitable substrate used in semiconductor, photovoltaic, flat panel, LCD-TFT, or MEMS device manufacturing. Examples of suitable substrates include without limitation, silicon substrates, silica substrates, silicon nitride substrates, silicon oxy nitride substrates, tungsten substrates, copper substrates, or combinations thereof. Additionally, substrates comprising tungsten or noble metals (e.g. platinum, palladium, rhodium, or gold) may be used. The substrate may also have one or more layers of differing materials already deposited upon it from a previous manufacturing step.

The temperature and the pressure within the reactor are held at conditions suitable for vapor deposition of at least part of the titanium-aluminum precursor onto the substrate. In other words, after introduction of the vaporized precursor into the chamber, conditions within the chamber are such that at least part of the vaporized precursor is deposited onto the substrate to form a metal-containing film. For instance, the pressure in the reactor may be held between about 0.1 Pa and about $10^5$ Pa, more preferably between about 2.5 Pa and about $10^3$ Pa, as required per the deposition parameters. Likewise, the temperature in the reactor may be held between about 20° C. and about 600° C., preferably between about 100° C. and about 400° C.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 350° C. Alternatively, when a thermal process is performed, the deposition temperature may range from approximately 200° C. to approximately 600° C.

In addition to the disclosed precursor, a reaction gas may also be introduced into the reactor. The reaction gas may be an oxidizing agent such as one of $O_2$; $O_3$; $H_2O$; $H_2O_2$; oxygen containing radicals such as O. or OH.; NO; $NO_2$; carboxylic acids such as formic acid, acetic acid, propionic acid; radical species of NO, $NO_2$, or the carboxylic acids; and mixtures thereof. Preferably, the oxidizing agent is selected from the group consisting of $O_2$, $O_3$, $H_2O$, $H_2O_2$, oxygen containing radicals thereof such as O. or OH., and mixtures thereof. Alternatively, the reaction gas may be a reducing agent such as one of $H_2$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1]nonane, dihydrobenzenfuran, pyrazoline, trimethylaluminum, dimethylzinc, diethylzinc, radical species thereof, and mixtures thereof. Preferably, the reducing agent is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof.

The reaction gas may be treated by a plasma, in order to decompose the reaction gas into its radical form. $N_2$ may also be utilized as a reducing agent when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

The vapor deposition conditions within the chamber allow the titanium-tetrahydroaluminate precursor and the reaction gas to react and form a titanium-aluminum-containing film on the substrate. In some embodiments, Applicants believe that plasma-treating the reaction gas may provide the reaction gas with the energy needed to react with the disclosed precursor.

Depending on what type of film is desired to be deposited, a second precursor may be introduced into the reactor. The second precursor comprises another element source, such as silicon, copper, praseodymium, manganese, iron, iridium, platinum, palladium, boron, gallium, ruthenium, titanium, tantalum, bismuth, zirconium, hafnium, lead, niobium, magnesium, aluminum, lanthanum, or mixtures of these. When a second precursor is utilized, the resultant film deposited on the substrate may contain at least 2 different elements.

The titanium-tetrahydroaluminate precursors and reaction gases may be introduced into the reactor either simultaneously (chemical vapor deposition), sequentially (atomic layer deposition) or different combinations thereof. The reactor may be purged with an inert gas between the introduction of the precursor and the introduction of the reaction gas. Alternatively, the reaction gas and the precursor may be mixed together to form a reaction gas/precursor mixture, and then introduced to the reactor in mixture form. Another example is to introduce the reaction gas continuously and to introduce the at least one titanium-tetrahydroaluminate precursor by pulse (pulsed chemical vapor deposition).

The vaporized precursor and the reaction gas may be pulsed sequentially or simultaneously (e.g. pulsed CVD) into the reactor. Each pulse of precursor may last for a time period ranging from about 0.01 seconds to about 10 seconds, alternatively from about 0.3 seconds to about 3 seconds, alternatively from about 0.5 seconds to about 2 seconds. In another embodiment, the reaction gas may also be pulsed into the reactor. In such embodiments, the pulse of each gas may last for a time period ranging from about 0.01 seconds to about 10 seconds, alternatively from about 0.3 seconds to about 3 seconds, alternatively from about 0.5 seconds to about 2 seconds.

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, depending on the specific deposition process. The deposition process may also be performed as many times as necessary to obtain the desired film.

In one non-limiting exemplary CVD type process, the vapor phase of the disclosed bimetallic titanium-tetrahydroaluminate precursor and a reaction gas are simultaneously introduced into the reactor. The two react to deposit at least part of the titanium-aluminum precursor on the substrate as the resulting titanium-aluminum containing thin film. When the reaction gas in this exemplary CVD process is treated with a plasma, the exemplary CVD process becomes an exemplary PECVD process. The reaction gas may be treated with plasma prior or subsequent to introduction into the chamber.

In one non-limiting exemplary ALD type process, the vapor phase of the disclosed bimetallic titanium-tetrahydroaluminate precursor is introduced into the reactor, where it is contacted with a suitable substrate. Excess precursor may then be removed from the reactor by purging and/or evacuating the reactor. A reducing agent (for example, $H_2$) is introduced into the reactor where it reacts with the absorbed precursor in a self-limiting manner. Any excess reducing agent is removed from the reactor by purging and/or evacuating the reactor. If the desired film is a titanium-aluminum alloy film, this two-step process may provide the desired film thickness or may be repeated until a film having the necessary thickness has been obtained.

Alternatively, if the desired film contains more than these two elements, the two-step process above may be followed by introduction of the vapor of a second precursor into the reactor. The second precursor will be selected based on the desired additional element(s) in the film being deposited. After introduction into the reactor, the second precursor is contacted with the substrate. Any excess second precursor is removed from the reactor by purging and/or evacuating the reactor. Once again, a reducing agent may be introduced into the reactor to react with the second precursor. Excess reducing agent is removed from the reactor by purging and/or evacuating the reactor. If a desired film thickness has been achieved, the process may be terminated. However, if a thicker film is desired, the entire four-step process may be repeated. By alternating the provision of the bimetallic titanium-tetrahydroaluminate precursor, second precursor, and reaction gas, a film of desired composition and thickness can be deposited.

When the reaction gas in this exemplary ALD process is treated with a plasma, the exemplary ALD process becomes an exemplary PEALD process. The reaction gas may be treated with plasma prior or subsequent to introduction into the chamber.

The titanium-aluminum-containing films resulting from the processes discussed above may include a pure titanium-aluminum (TiAl), titanium-aluminum nitride (TiAlN), titanium-aluminum carbide (TiAlC), titanium-aluminum carbonitride (TiAlCN), titanium-aluminum silicide ($(TiAl)_kSi_l$), titanium-aluminum siliconitride ($(TiAl)_kSi_lN$), titanium-aluminum boron ($(TiAl)_kB_l$), titanium-aluminum boron nitride ($(TiAl)_kB_lN$), or titanium-aluminum oxide ($(TiAl)_nO_m$) film, wherein k, l, m, and n are integers which inclusively range from 1 to 6. One of ordinary skill in the art will recognize that by judicial selection of the appropriate titanium-tetrahydroaluminuate precursor, optional second precursors, and reaction gas species, the desired film composition may be obtained.

EXAMPLES

The following non-limiting examples are provided to further illustrate embodiments of the invention. However, the examples are not intended to be all inclusive and are not intended to limit the scope of the inventions described herein.

Example 1

Prophetic Synthesis of $Ti(AlH_4)_3(dme)$

Add $TiCl_4$ into the solution of $NaAlH_4$ or $LiAlH_4$ in 1,2-dimethoxyethane (dme) cooled at −78 C and stirred for 48 h at 25 C followed by crystallization from $Et_2O$ (or toluene) gives $Ti(AlH_4)_3(dme)$.

Example 1'

Prophetic Synthesis of $Ti(AlH_4)_3(THF)_2$ $Ti(AlH_4)_3(THF)_2$ could be obtained from the same synthesis method described in Example 1. The molecule can also be obtained from $Ti(OPr-iso)_4$ and $Al_2H_6$ in THF.

Example 2

Prophetic Synthesis of $Ti(AlH_4)_2(iPr_2-DAD)$

Granules of lithium are added to a solution of the $iPr_2$-DAD compound in diethyl ether cooled at −78 C and stirred until the end of the reaction at 25 C for 12 hours (generation of a red color product). Then a solution of $TiCl_4$ (same quantity as $iPr_2$-DAD) in n-hexane is added dropwise to the solution of $iPr_2$-DAD at −78 C (formation of a brown precipitate). Then the solution is stirred for 2 hr at 25 C, cooled again to −78 C and reacted with two equivalents of $Li(AlH_4)$ in diethyl ether (immediate red coloration). After allowing warming to 25 C and under stirring for 24 hr, the solvent is removed and the residue is purified. The final product $Ti(AlH_4)_2(iPr_2-dad)$ is obtained as a reddish liquid and its structure confirmed by NMR.

Example 3

Prophetic Synthesis of $Ti(AlH_4)(iPr_2-DAD)_2$

Granules of lithium are added to a solution of the $iPr_2$-DAD compound in diethyl ether cooled at −78 C and stirred at 25 C for 12 hours until the end of the reaction (generation of a red color product). Then a solution of $TiCl_4$ (half-molar equivalent of $iPr_2$-DAD) in n-hexane is added dropwise (formation of a brown precipitate). Then the solution is stirred for 2 hr at 25 C, cooled again to −78 C and reacted with two equivalents of Li(AlH$_4$) in diethyl ether (immediate red coloration). After allowing warming to 25 C and under stirring for 24 hr, the solvent is removed and the residue is purified. The final product Ti(AlH$_4$)(iPr$_2$-DAD)$_2$ is obtained as confirmed by NMR.

Example 4

Prophetic Synthesis of Ti(AlH$_4$)(Me$_2$-NHCs)$_2$

Into the solution of the Me$_2$-NHCs (1,3-dimethylimidazoline-2-ylidene) compound in THF, a solution of TiCl$_4$ (half-molar equivalent of Me$_2$-NHCs) in n-hexane is added dropwise at −78 C and stirred at 25 C for 12 hours. Then the solution is cooled again to −78 C and reacted with two equivalents of Li(AlH$_4$) in diethyl ether (immediate red coloration). After allowing warming to 25 C and under stirring for 24 hr, the solvent is removed and the residue is purified. The final product Ti(AlH$_4$)(Me$_2$-NHCs)$_2$ is obtained as confirmed by NMR.

Example 5

Prophetic Deposition of Thin TiAl Films Using Ti(AlH$_4$)$_2$(iPr$_2$-DAD)

Ti(AlH$_4$)$_2$(iPr$_2$-DAD) was synthesized as described in Example 2. It is expected to obtain TiAl films using this molecule and the following example describes one way, among others, to deposit such films.

Ti(AlH$_4$)$_2$(iPr$_2$-DAD) is placed in a canister. Vapors of Ti(AlH$_4$)$_2$(iPr$_2$-DAD) are transported to the reaction furnace by flowing nitrogen as a carrier gas within the heated canister in order to provide enough vapor. Hydrogen is introduced into the deposition system to react with the titanium-aluminum vapors at the surface of the wafer in an CVD scheme (simultaneous introduction of precursors' vapors). Hydrogen (H$_2$) is believed to be a molecule of choice, but any type of reducing agent may be selected. Alternatively, depending on process conditions, inert gases such as nitrogen, argon, of helium, can be used. TiAl films are supposedly obtained from temperatures as low as 150° C. Analytical results show that the TiAl films are very pure, with very low carbon contamination. In order to improve the quality of the films, some post-treatments such as annealing can be performed. A typical example being to heat at a temperature equal to or higher than the deposition temperature within an inert atmosphere or using reactive gases such as hydrogen.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A method of depositing a titanium-aluminum containing film, the method comprising:
   introducing at least one titanium-tetrahydroaluminate precursor into a reactor having at least one substrate disposed therein, the at least one titanium-tetrahydroaluminate precursor being selected from the group consisting of:
   (i) Ti(AlH$_4$)$_3$—X$_n$
   wherein
   0<n≤2; and X is selected among:
      compounds of N, P, As, Sb or Bi in oxidation state 3;
      compounds of O, S, Se or Te in oxidation state 2;
      carbon monoxide, aromatic hydrocarbons, or dichloromethane;
   (ii) Ti(AlH$_4$)$_2$L, wherein L is selected from the group consisting of pentadienyl, cyclopentadienyl, hexadienyl, cyclohexadienyl, allyl, diimine (DAD), N-heterocyclic carbenes (NHCs), amidinate, silyl-amidinate, formamidinate, dialkylethylenediamine (R1N—CH$_2$—CH$_2$—NR2), dialkylaminoalkylborane (R1N—BR2-NR3), dialkylaminoalkylalane (R1N—AlR2-NR3), dialkylaminoalkylgallium (R1N—GaR2-NR3), β-acetylacetonate, β-diketonate, β-diketimine, and pyrrolecarbaldiminate;
   (iii) Ti(AlH$_4$)L$^1$L$^2$, wherein each of L$^1$ and L$^2$ is independently selected from the group consisting of pentadienyl, cyclopentadienyl, hexadienyl, cyclohexadienyl, allyl, diimine (DAD), N-heterocyclic carbenes (NHCs), amidinate, silyl-amidinate, formamidinate, dialkylethylenediamine (R1N—CH$_2$—CH$_2$—NR2), dialkylaminoalkylborane (R1N—BR2-NR3), dialkylaminoalkylalane (R1N—AlR2-NR3), dialkylaminoalkylgallium (R1N—GaR2-NR3), β-acetylacetonate, β-diketonate, β-diketimine, and pyrrolecarbaldiminate, wherein L$^1$ and L$^2$ do not both equal non-substituted cyclopentadienyl ligands;
   depositing at least part of the titanium-tetrahydroaluminate precursor onto the at least one substrate to form the titanium-aluminum containing film.

2. The method of claim 1, wherein the titanium-tetrahydroaluminate precursor of formula (i) is selected from the group consisting of Ti(AlH$_4$)$_3$-(methanol)$_n$, Ti(AlH$_4$)$_3$-(ethanol)$_n$, Ti(AlH$_4$)$_3$-(n-propanol)$_n$, Ti(AlH$_4$)$_3$-(i-propanol)$_n$, Ti(AlH$_4$)$_3$-(ethylene oxide)$_n$, Ti(AlH$_4$)$_3$-(dimethylether)$_n$, Ti(AlH$_4$)$_3$-(diethylether)$_n$, Ti(AlH$_4$)$_3$-(dimethoxymethane)$_n$, Ti(AlH$_4$)$_3$-(dimethoxyethane)$_n$, Ti(AlH$_4$)$_3$-(acetone)$_n$, Ti(AlH$_4$)$_3$-(THF)$_n$, Ti(AlH$_4$)$_3$-(methyl-THF)$_n$, Ti(AlH$_4$)$_3$-(benzene)$_n$, Ti(AlH$_4$)$_3$-(toluene)$_n$, Ti(AlH$_4$)$_3$-(mesitylene)$_n$, Ti(AlH$_4$)$_3$-(methoxybenzene)$_n$, Ti(AlH$_4$)$_3$-(dimethoxybenzene)$_n$, Ti(AlH$_4$)$_3$-(diglyme)$_n$, Ti(AlH$_4$)$_3$-(triglyme)$_n$, Ti(AlH$_4$)$_3$-(tetraglyme)$_n$, Ti(AlH$_4$)$_3$-(pyridine)$_n$, Ti(AlH$_4$)$_3$-(1-methylpyridine)$_n$, Ti(AlH$_4$)$_3$-(2-methylpyridine)$_n$, Ti(AlH$_4$)$_3$-(3-methylpyridine)$_n$, Ti(AlH4)$_3$-(bipyridine)$_n$, Ti(AlH$_4$)$_3$-(pyridazine)$_n$, Ti(AlH$_4$)$_3$-(pyrimidine)$_n$, Ti(AlH$_4$)$_3$-(pyrazine)$_n$, Ti(AlH$_4$)$_3$-(Me$_3$N)$_n$, Ti(AlH$_4$)$_3$-(tBuMe$_2$N)$_n$, Ti(AlH$_4$)$_3$-(Et$_3$N)$_n$, Ti(AlH$_4$)$_3$-(nPr$_3$N)$_n$, Ti(AlH$_4$)$_3$-(iPr$_3$N)$_n$, Ti(AlH$_4$)$_3$-(Me$_2$NH)$_n$, Ti(AlH$_4$)$_3$-(Et$_2$NH)$_n$, Ti(AlH$_4$)$_3$-(iPr$_2$NH)$_n$, Ti(AlH$_4$)$_3$-(nPr$_2$NH)$_n$, Ti(AlH$_4$)$_3$-(MeNH$_2$)$_n$, Ti(AlH$_4$)$_3$-(EtNH$_2$)$_n$, Ti(AlH$_4$)$_3$-(nPrNH$_2$)$_n$, Ti(AlH$_4$)$_3$-(iPrNH$_2$)$_n$, Ti(AlH$_4$)$_3$-(Me$_3$P)$_n$, Ti(AlH$_4$)$_3$-(tBuMe$_2$P)$_n$, Ti(AlH$_4$)$_3$-(Et$_3$P)$_n$, Ti(AlH$_4$)$_3$-(nPr$_3$P)$_n$, Ti(AlH$_4$)$_3$-(iPr$_3$P)$_n$, Ti(AlH$_4$)$_3$-(Me$_2$PH)$_n$, Ti(AlH$_4$)$_3$-(Et$_2$PH)$_n$, Ti(AlH$_4$)$_3$-(iPr$_2$PH)$_n$, Ti(AlH$_4$)$_3$-(nPr$_2$PH)$_n$, Ti(AlH$_4$)$_3$-(MePH$_2$)$_n$, Ti(AlH$_4$)$_3$-(EtPH$_2$)$_n$, Ti(AlH$_4$)$_3$-(nPrPH$_2$)$_n$, Ti(AlH$_4$)$_3$-(iPrPH$_2$)$_n$, Ti(AlH$_4$)$_3$-(Me$_3$As)$_n$, Ti(AlH$_4$)$_3$-(tBuMe$_2$As)$_n$, Ti(AlH$_4$)$_3$-(Et$_3$As)$_n$, Ti(AlH$_4$)$_3$-(nPr$_3$As)$_n$, Ti(AlH$_4$)$_3$-(iPr$_3$As)$_n$, Ti(AlH$_4$)$_3$-(Me$_2$AsH)$_n$, Ti(AlH$_4$)$_3$-(Et$_2$AsH)$_n$, Ti(AlH$_4$)$_3$-(iPr$_2$AsH)$_n$, Ti(AlH$_4$)$_3$-(nPr$_2$AsH)$_n$, Ti(AlH$_4$)$_3$-(MeAsH$_2$)$_n$, Ti(AlH$_4$)$_3$-(EtAsH$_2$)$_n$, Ti(AlH$_4$)$_3$-(nPrAsH$_2$)$_n$, and Ti(AlH$_4$)$_3$-(iPrAsH$_2$)$_n$.

3. The method of claim 1, wherein the titanium-tetrahydroaluminate precursor of formula (ii) is selected from the group consisting of Ti(AlH$_4$)$_2$(H$_2$-DAD)), Ti(AlH$_4$)$_2$(Me$_2$-DAD), Ti(AlH$_4$)$_2$(Et$_2$-DAD), Ti(AlH$_4$)$_2$(iPr$_2$-DAD), Ti(AlH$_4$)$_2$(nPr$_2$-DAD), Ti(AlH$_4$)$_2$(nBu$_2$-DAD), Ti(AlH$_4$)$_2$(sBu$_2$-DAD), Ti(AlH$_4$)$_2$(iBu$_2$-DAD), Ti(AlH$_4$)$_2$(tBu$_2$-

DAD), Ti(AlH₄)₂(iPr₂-MDAD), Ti(AlH₄)₂(Me₂-DMDAD), Ti(AlH₄)₂(iPr₂-DMDAD), Ti(AlH₄)₂(H₂-fAM), Ti(AlH₄)₂(Me₂-fAMD), Ti(AlH₄)₂(Et₂-fAMD), Ti(AlH₄)₂(iPr₂-fAMD), Ti(AlH₄)₂(nPr₂-fAMD), Ti(AlH₄)₂(nBu₂-fAMD), Ti(AlH₄)₂(iBu₂-fAMD), Ti(AlH₄)₂(tBu₂-fAMD), Ti(AlH₄)₂(sBu₂-fAMD), Ti(AlH₄)₂(H₂-AMD), Ti(AlH₄)₂(Me₂-AMD), Ti(AlH₄)₂(Et₂-AMD), Ti(AlH₄)₂(iPr₂-AMD), Ti(AlH₄)₂(nPr₂-AMD), Ti(AlH₄)₂(tBu₂-AMD), Ti(AlH₄)₂(nBu₂-AMD), Ti(AlH₄)₂(sBu₂-AMD), Ti(AlH₄)₂(iBu₂-AMD), Ti(AlH₄)₂(H₂—SiAMD), Ti(AlH₄)₂(Me₂-SiAMD), Ti(AlH₄)₂(Et₂-SiAMD), Ti(AlH₄)₂(iPr₂—SiAMD), Ti(AlH₄)₂(nPr₂—SiAMD), Ti(AlH₄)₂(tBu₂-SiAMD), Ti(AlH₄)₂(nBu₂-SiAMD), Ti(AlH₄)₂(sBu₂-SiAMD), Ti(AlH₄)₂(iBu₂-SiAMD), Ti(AlH₄)₂(H₂-NacNac), Ti(AlH₄)₂(Me₂-NacNac), Ti(AlH₄)₂(Et₂-NacNac), Ti(AlH₄)₂(iPr₂-NacNac), Ti(AlH₄)₂(nPr₂-NacNac), Ti(AlH₄)₂(tBu₂-NacNac), Ti(AlH₄)₂(nBu₂-NacNac), Ti(AlH₄)₂(sBu₂-NacNac), Ti(AlH₄)₂(iBu₂-NacNac), Ti(AlH₄)₂(H-acNac), Ti(AlH₄)₂(Me-acNac), Ti(AlH₄)₂(Et-acNac), Ti(AlH₄)₂(iPr-acNac), Ti(AlH₄)₂(nPr-acNac), Ti(AlH₄)₂(tBu-acNac), Ti(AlH₄)₂(nBu-acNac), Ti(AlH₄)₂(sBu-acNac), Ti(AlH₄)₂(iBu-acNac), Ti(AlH₄)₂(acac), Ti(AlH₄)₂Cp, Ti(AlH₄)₂(Me-Cp), Ti(AlH₄)₂(Et-Cp), Ti(AlH₄)₂(iPr-Cp), Ti(AlH₄)₂(Me₃-Cp), Ti(AlH₄)₂(Me₄-Cp), Ti(AlH₄)₂(Me₅-Cp), Ti(AlH₄)₂(iPr₃-Cp), Ti(AlH₄)₂(tBu₃-Cp), Ti(AlH₄)₂Op, Ti(AlH₄)₂(Me-Op), Ti(AlH₄)₂(Et-Op), Ti(AlH₄)₂(iPr-Op), Ti(AlH₄)₂(Me₃-Op), Ti(AlH₄)₂(Me₄-Op), Ti(AlH₄)₂(Me₅-Op), Ti(AlH₄)₂(iPr₃-Op), Ti(AlH₄)₂(tBu₃-Op), Ti(AlH₄)₂(CHDI), Ti(AlH₄)₂(Me-CHDI), Ti(AlH₄)₂(Et-CHDI), Ti(AlH₄)₂(iPr-CHDI), Ti(AlH₄)₂(Me₃-CHDI), Ti(AlH₄)₂(Me₄CHDI), Ti(AlH₄)₂(Me₅-CHDI), Ti(AlH₄)₂(iPr₃-CHDI), Ti(AlH₄)₂(tBu₃-CHDI), Ti(AlH₄)₂(HDI), Ti(AlH₄)₂(Me-HDI), Ti(AlH₄)₂(Et-HDI), Ti(AlH₄)₂(iPr-HDI), Ti(AlH₄)₂(Me₃-HDI), Ti(AlH₄)₂(Me₄-HDI), Ti(AlH₄)₂(Me₅-HDI), Ti(AlH₄)₂(iPr₃-HDI), Ti(AlH₄)₂(tBu₃HDI), Ti(AlH₄)₂(allyl), Ti(AlH₄)₂(Me-allyl), Ti(AlH₄)₂(Et-allyl), Ti(AlH₄)₂(iPr-allyl), Ti(AlH₄)₂(Me₂-allyl), Ti(AlH₄)₂(Me₃-allyl), Ti(AlH₄)₂(Me₂-DAAB), Ti(AlH₄)₂(Et₂-DAAB), Ti(AlH₄)₂(iPr₂-DAAB), Ti(AlH₄)₂(nPr₂-DAAB), Ti(AlH₄)₂(tBu₂-DAAB), Ti(AlH₄)₂(nBu₂-DAAB), Ti(AlH₄)₂(sBu₂-DAAB), Ti(AlH₄)₂(iBu₂-DAAB), Ti(AlH₄)₂(MeEt-DAAB), Ti(AlH₄)₂(Me₂-DAAA), Ti(AlH₄)₂(Et₂-DAAA), Ti(AlH₄)₂(iPr₂-DAAA), Ti(AlH₄)₂(nPr₂-DAAA), Ti(AlH₄)₂(tBu₂-DAAA), Ti(AlH₄)₂(nBu₂-DAAA), Ti(AlH₄)₂(sBu₂-DAAA), Ti(AlH₄)₂(iBu₂-DAAA), Ti(AlH₄)₂(MeEt-DAAA), Ti(AlH₄)₂(Me₂-DAAG), Ti(AlH₄)₂(Et₂-DAAG), Ti(AlH₄)₂(iPr₂-DAAG), Ti(AlH₄)₂(nPr₂-DAAG), Ti(AlH₄)₂(tBu₂-DAAG), Ti(AlH₄)₂(nBu₂-DAAG), Ti(AlH₄)₂(sBu₂-DAAG), Ti(AlH₄)₂(iBu₂-DAAG), Ti(AlH₄)₂(MeEt-DAAG), Ti(AlH₄)₂(Me₂-EDA), Ti(AlH₄)₂(Et₂-EDA), Ti(AlH₄)₂(iPr₂-EDA), Ti(AlH₄)₂(nPr₂-EDA), Ti(AlH₄)₂(nBu₂-EDA), Ti(AlH₄)₂(tBu₂-EDA), Ti(AlH₄)₂(sBu₂-EDA), Ti(AlH₄)₂(iBu₂-EDA), Ti(AlH₄)₂(MeEt-EDA), Ti(AlH₄)₂(Me-PCAI), Ti(AlH₄)₂(Et-PCAI), Ti(AlH₄)₂(iPr-PCAI), Ti(AlH₄)₂(Me₂-NHCs), Ti(AlH₄)₂(Et₂-NHCs), Ti(AlH₄)₂(nPr₂-NHCs), Ti(AlH₄)₂(iPr₂-NHCs), Ti(AlH₄)₂(nBu₂-NHCs), Ti(AlH₄)₂(tBu₂-NHCs), Ti(AlH₄)₂(TMS₂—NHCs), and Ti(AlH₄)₂(Me₂-Me₂NHCs).

4. The method of claim 1, wherein the titanium-tetrahydroaluminate precursor of formula (iii) is selected from the group consisting of Ti(AlH₄)(H₂-DAD)₂, Ti(AlH₄)(Me₂-DAD)₂, Ti(AlH₄)(Et₂-DAD)₂, Ti(AlH₄)(iPr₂-DAD)₂, Ti(AlH₄)(nPr₂-DAD)₂, Ti(AlH₄)(nBu₂-DAD)₂, Ti(AlH₄)(sBu₂-DAD)₂, Ti(AlH₄)(iBu₂-DAD)₂, Ti(AlH₄)(tBu₂-DAD)₂, Ti(AlH₄)(iPr₂-MDAD)₂, Ti(AlH₄)(Me₂-DMDAD)₂, Ti(AlH₄)(iPr₂-DMDAD)₂, Ti(AlH₄)(H₂-fAMD)₂, Ti(AlH₄)(Me₂-fAMD)₂, Ti(AlH₄)(Et₂-fAMD)₂, Ti(AlH₄)(iPr₂-fAMD)₂, Ti(AlH₄)(nPr₂-fAMD)₂, Ti(AlH₄)(nBu₂-fAMD)₂, Ti(AlH₄)(iBu₂-fAMD)₂, Ti(AlH₄)(tBu₂-fAMD)₂, Ti(AlH₄)(sBu₂-fAMD)₂, Ti(AlH₄)(H₂-AMD)₂, Ti(AlH₄)(Me₂-AMD)₂, Ti(AlH₄)(Et₂-AMD)₂, Ti(AlH₄)(iPr₂-AMD)₂, Ti(AlH₄)(nPr₂-AMD)₂, Ti(AlH₄)(tBu₂-AMD)₂, Ti(AlH₄)(nBu₂-AMD)₂, Ti(AlH₄)(sBu₂-AMD)₂, Ti(AlH₄)(iBu₂-AMD)₂, Ti(AlH₄)(H₂—SiAMD)₂, Ti(AlH₄)(Me₂-SIAMD)₂, Ti(AlH₄)(Et₂-SiAMD)₂, Ti(AlH₄)(iPr₂—SiAMD)₂, Ti(AlH₄)(nPr₂—SiAMd)₂, Ti(AlH₄)(tBu₂-SiAMD)₂, Ti(AlH₄)(nBu₂-SiAMD)₂, Ti(AlH₄)(sBu₂-SiAMD)₂, Ti(AlH₄)(iBu₂-SiAMD)₂, Ti(AlH₄)(H₂-NacNac)₂, Ti(AlH₄)(Me₂-NacNac)₂, Ti(AlH₄)(Et₂-NacNac)₂, Ti(AlH₄)(iPr₂-NacNac)₂, Ti(AlH₄)(nPr₂-NacNac)₂, Ti(AlH₄)(tBu₂-NacNac)₂, Ti(AlH₄)(nBu₂-NacNac)₂, Ti(AlH₄)(sBu₂-NacNac)₂, Ti(AlH₄)(iBu₂-NacNac)₂, Ti(AlH₄)(H-acNac)₂, Ti(AlH₄)(Me-acNac)₂, Ti(AlH₄)(Et-acNac)₂, Ti(AlH₄)(iPr-acNac)₂, Ti(AlH₄)(nPr-acNac)₂, Ti(AlH₄)(tBu-acNac)₂, Ti(AlH₄)(nBu-acNac)₂, Ti(AlH₄)(sBu-acNac)₂, Ti(AlH₄)(iBu-acNac)₂, Ti(AlH₄)(acac)₂, Ti(AlH₄)Cp₂, Ti(AlH₄)(Me-Cp)₂, Ti(AlH₄)(Et-Cp)₂, Ti(AlH₄)(iPr-Cp)₂, Ti(AlH₄)(Me₃-Cp)₂, Ti(AlH₄)(Me₄-Cp)₂, Ti(AlH₄)(Me₅-Cp)₂, Ti(AlH₄)(iPr₃-Cp)₂, Ti(AlH₄)(tBu₃-Cp)₂, Ti(AlH₄)Op₂, Ti(AlH₄)(Me-Op)₂, Ti(AlH₄)(Et-Op)₂, Ti(AlH₄)(iPr-Op)₂, Ti(AlH₄)(Me₃-Op)₂, Ti(AlH₄)(Me₄-Op)₂, Ti(AlH₄)(Me₅-Op)₂, Ti(AlH₄)(iPr₃-Op)₂, Ti(AlH₄)(tBu₃-Op)₂, Ti(AlH₄)(CHDI)₂, Ti(AlH₄)(Me-CHDI)₂, Ti(AlH₄)(Et-CHDI)₂, Ti(AlH₄)(iPr-CHDI)₂, Ti(AlH₄)(Me₃-CHDI)₂, Ti(AlH₄)(Me₄-CHDI)₂, Ti(AlH₄)(Me₅-CHDI)₂, Ti(AlH₄)(iPr₃-CHDI)₂, Ti(AlH₄)(tBu₃-CHDI)₂, Ti(AlH₄)(HDI)₂, Ti(AlH₄)(Me-HDI)₂, Ti(AlH₄)(Et-HDI)₂, Ti(AlH₄)(iPr-HDI)₂, Ti(AlH₄)(Me₃-HDI)₂, Ti(AlH₄)(Me₄-HDI)₂, Ti(AlH₄)(Me₅-HDI)₂, Ti(AlH₄)(iPr₃-HDI)₂, Ti(AlH₄)(tBu₃-HDI)₂, Ti(AlH₄)(allyl)₂, Ti(AlH₄)(Me-allyl)₂, Ti(AlH₄)(Et-allyl)₂, Ti(AlH₄)(iPr-allyl)₂, Ti(AlH₄)(Me₂-allyl)₂, Ti(AlH₄)(Me₃-allyl)₂, Ti(AlH₄)(Me₂-DAAB)₂, Ti(AlH₄)(Et₂-DAAB)₂, Ti(AlH₄)(iPr₂-DAAB)₂, Ti(AlH₄)(nPr₂-DAAB)₂, Ti(AlH₄)(tBu₂-DAAB)₂, Ti(AlH₄)(nBu₂-DAAB)₂, Ti(AlH₄)(sBu₂-DAAB)₂, Ti(AlH₄)(iBu₂-DAAB)₂, Ti(AlH₄)(MeEt-DAAB)₂, Ti(AlH₄)(Me₂-DAAA)₂, Ti(AlH₄)(Et₂-DAAA)₂, Ti(AlH₄)(iPr₂-DAAA)₂, Ti(AlH₄)(nPr₂-DAAA)₂, Ti(AlH₄)(tBu₂-DAAA)₂, Ti(AlH₄)(nBu₂-DAAA)₂, Ti(AlH₄)(sBu₂-DAAA)₂, Ti(AlH₄)(iBu₂-DAAA)₂, Ti(AlH₄)(MeEt-DAAA)₂, Ti(AlH₄)(Me₂-DAAG)₂, Ti(AlH₄)(Et₂-DAAG)₂, Ti(AlH₄)(iPr₂-DAAG)₂, Ti(AlH₄)(nPr₂-DAAG)₂, Ti(AlH₄)(tBu₂-DAAG)₂, Ti(AlH₄)(nBu₂-DAAG)₂, Ti(AlH₄)(sBu₂-DAAG)₂, Ti(AlH₄)(iBu₂-DAAG)₂, Ti(AlH₄)(MeEt-DAAG)₂, Ti(AlH₄)(Me₂-EDA)₂, Ti(AlH₄)(Et₂-EDA)₂, Ti(AlH₄)(iPr₂-EDA)₂, Ti(AlH₄)(nPr₂-EDA)₂, Ti(AlH₄)(nBu₂-EDA)₂, Ti(AlH₄)(tBu₂-EDA)₂, Ti(AlH₄)(sBu₂-EDA)₂, Ti(AlH₄)(iBu₂-EDA)₂, Ti(AlH₄)(MeEt-EDA)₂, Ti(AlH₄)(Me-PCAI)₂, Ti(AlH₄)(Et-PCAI)₂, Ti(AlH₄)(iPr-PCAI)₂, Ti(AlH₄)(Me₂-NHCs)₂, Ti(AlH₄)(Et₂-NHCs)₂, Ti(AlH₄)(nPr₂-NHCs)₂, Ti(AlH₄)(iPr₂-NHCs)₂, Ti(AlH₄)(nBu₂-NHCs)₂, Ti(AlH₄)(tBu₂-NHCs)₂, Ti(AlH₄)(TMS₂—NHCs)₂, and Ti(AlH₄)(Me₂-Me₂NHCs)₂.

5. The method of claim 1, wherein the method is performed at a temperature between about 20° C. and about 800° C.

6. The method of claim 1, wherein the method is performed at a pressure between about 0.1 Pa and about 10⁵ Pa.

7. The method of claim 1, wherein the deposition method is selected from the group consisting of chemical vapor deposition (CVD), atomic layer deposition (ALD), plasma CVD, plasma ALD, pulse CVD, low pressure CVD, subatmospheric CVD, and atmospheric pressure CVD.

8. The method of claim 1, wherein the titanium-aluminum containing film is selected from the group consisting of pure titanium-aluminum (TiAl), titanium-aluminum nitride (TiAlN), titanium-aluminum carbide (TiAlC), titanium-aluminum carbonitride (TiAlCN), titanium-aluminum silicide ((TiAl)Si), titanium-aluminum siliconitride ((TiAl)SiN), titanium-aluminum boron ((TiAl)B), titanium-aluminum boron nitride ((TiAl)BN), titanium-aluminum oxide (TiAlO), and titanium-aluminum nitroxide (TiAlNO).

9. The method of claim 1, further comprising:
introducing a reaction gas into the reactor at the same time or at an alternate time as the introduction of the titanium-tetrahydroaluminate precursor;
wherein at least part of the titanium-tetrahydroaluminate precursor is deposited onto the at least one substrate to form the titanium-aluminum containing film by reacting the reaction gas with the titanium-tetrahydroaluminate precursor.

10. The method of claim 9, wherein the reaction gas is a reducing agent.

11. The method of claim 10, wherein the reducing agent is selected from the group consisting of: $N_2$, $H_2$; $SiH_4$; $Si_2H_6$; $Si_3H_8$; $NH_3$; $(CH_3)_2SiH_2$; $(C_2H_5)_2SiH_2$; $(CH_3)SiH_3$; $(C_2H_5)SiH_3$; phenyl silane; $N_2H_4$; $N(SiH_3)_3$; $N(CH_3)H_2$; $N(C_2H_5)H_2$; $N(CH_3)_2H$; $N(C_2H_5)_2H$; $N(CH_3)_3$; $N(C_2H_5)_3$; $(SiMe_3)_2NH$; $(CH_3)HNNH_2$; $(CH_3)_2NNH_2$; phenyl hydrazine; $B_2H_6$; 9-borabicyclo[3,3,1]nonane; dihydrobenzenfuran; pyrazoline; trimethylaluminum; dimethylzinc; diethylzinc; radical species thereof; and mixtures thereof.

12. The method of claim 9, wherein the reaction gas is an oxidizing agent.

13. The method of claim 12, wherein the oxidizing agent is selected from the group consisting of: $O_2$; $O_3$; $H_2O$; $H_2O_2$; NO; $NO_2$; carboxylic acids; radical species thereof; and mixtures thereof.

14. The method of claim 4, wherein the titanium-tetrahydroaluminate precursor of formula (iii) is selected from the group consisting of $Ti(AlH_4)Cp_2$, $Ti(AlH_4)(Me-Cp)_2$, $Ti(AlH_4)(Et-Cp)_2$, $Ti(AlH_4)(iPr-Cp)_2$, $Ti(AlH_4)(Me_3-Cp)_2$, $Ti(AlH_4)(Me_4-Cp)_2$, $Ti(AlH_4)(Me_5-Cp)_2$, $Ti(AlH_4)(iPr_3-Cp)_2$, and $Ti(AlH_4)(tBu_3-Cp)_2$.

15. The method of claim 14, wherein the reaction gas is a reducing agent.

16. The method of claim 15, wherein the reducing agent is selected from the group consisting of: $N_2$, $H_2$; $SiH_4$; $Si_2H_6$; $Si_3H_8$; $NH_3$; $(CH_3)_2SiH_2$; $(C_2H_5)_2SiH_2$; $(CH_3)SiH_3$; $(C_2H_5)SiH_3$; phenyl silane; $N_2H_4$; $N(SiH_3)_3$; $N(CH_3)H_2$; $N(C_2H_5)H_2$; $N(CH_3)_2H$; $N(C_2H_5)_2H$; $N(CH_3)_3$; $N(C_2H_5)_3$; $(SiMe_3)_2NH$; $(CH_3)HNNH_2$; $(CH_3)_2NNH_2$; phenyl hydrazine; $B_2H_6$; 9-borabicyclo[3,3,1]nonane; dihydrobenzenfuran; pyrazoline; trimethylaluminum; dimethylzinc; diethylzinc; radical species thereof; and mixtures thereof.

* * * * *